US011103618B2

(12) United States Patent
Kalpakci et al.

(10) Patent No.: US 11,103,618 B2
(45) Date of Patent: Aug. 31, 2021

(54) DEMINERALIZED BONE MATRIX HAVING IMPROVED HANDLING CHARACTERISTICS

(71) Applicant: Warsaw Orthopedic, Inc., Warsaw, IN (US)

(72) Inventors: Kerem N. Kalpakci, Memphis, TN (US); Daniel A. Shimko, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 15/902,038

(22) Filed: Feb. 22, 2018

(65) Prior Publication Data

US 2019/0255216 A1 Aug. 22, 2019

(51) Int. Cl.

*A61L 27/36* (2006.01)
*A61L 27/12* (2006.01)
*A61L 27/14* (2006.01)
*A61L 27/20* (2006.01)
*A61L 27/50* (2006.01)
*A61L 27/54* (2006.01)
*A61L 27/58* (2006.01)
*A61L 27/48* (2006.01)

(52) U.S. Cl.

CPC ........... *A61L 27/3608* (2013.01); *A61L 27/12* (2013.01); *A61L 27/14* (2013.01); *A61L 27/20* (2013.01); *A61L 27/48* (2013.01); *A61L 27/50* (2013.01); *A61L 27/54* (2013.01); *A61L 27/58* (2013.01); *A61L 2400/06* (2013.01); *A61L 2400/12* (2013.01); *A61L 2430/02* (2013.01)

(58) Field of Classification Search

None

See application file for complete search history.

(56) References Cited

U.S. PATENT DOCUMENTS 5,385,887 A 1/1995 Yim et al.
5,422,340 A 6/1995 Ammann et al.
6,911,212 B2 * 6/2005 Gertzman .............. A61K 35/32 424/426
7,019,192 B2 * 3/2006 Gertzman ................. C08L 5/08 623/16.11
7,582,309 B2 9/2009 Rosenberg et al.
7,790,699 B2 * 9/2010 Melvik ................ A61K 9/1652 514/54
8,357,384 B2 * 1/2013 Behnam .............. A61L 27/3604 424/422
8,697,107 B2 4/2014 Drapeau et al.
9,358,323 B2 6/2016 Shimko
2003/0180376 A1 9/2003 Dalal et al.
2005/0177245 A1 8/2005 Leatherbury et al.
2007/0225811 A1 9/2007 Scifert et al.
2008/0147197 A1 6/2008 McKay
2008/0152691 A1 6/2008 Drapeau et al.
2009/0149873 A1 6/2009 Zhou et al.
2009/0238758 A1 9/2009 Wellisz et al.
2010/0098762 A1 4/2010 Han et al.
2012/0107383 A1 * 5/2012 McKay .................. A61K 31/22 424/423
2013/0287817 A1 10/2013 Drapeau et al.

FOREIGN PATENT DOCUMENTS

WO 2008157495 A2 12/2008

OTHER PUBLICATIONS

ALGISORB Calcium Alginate Dressing (date unknown). Retrieved Dec. 27, 2013, from http://www.skawamoto.com/Upload/Products/200810993631288.pdf. 1 page.

Augst et al. Alginate hydrogels as biomaterials. Macromol Biosci. Aug. 7, 2006;6(8):623-33. 11 pages.

Clokie CM, Urist MR. Bone morphogenetic protein excipients: comparative observations on poloxamer. Plast Reconstr Surg. Feb. 2000;105(2):628-37. 10 pages.

Author Corrections, in: J Craniofac Surg. May 2008;19(3):871. 1 page.

Fowler et al. Evaluation of pluronic polyols as carriers for grafting materials: study in rat calvaria defects. J Periodontol. Feb. 2002;73(2):191-7. 7 pages.

Gombotz et al. Protein release from alginate matrices. Adv Drug Deliv Rev. May 4, 1998;31(3):267-285. 19 pages.

Luginbuehl et al. Insulin-like growth factor I-releasing alginate-tricalciumphosphate composites for bone regeneration. Pharm Res. Jun. 2005;22(6):940-50. Epub Jun. 8, 2005. 11 pages.

Poloxamer 407. (Mar. 7, 2013). In Wikipedia, The Free Encyclopedia. Retrieved 02:07, Dec. 27, 2013, from http://en.wikipedia.org/w/index.php?title=Poloxamer.sub.--407&oldid=54255- 1598. 2 pages.

Zhou et al. An evaluation of hydroxyapatite and biphasic calcium phosphate in combination with Pluronic F127 and BMP on bone repair. J Craniofac Surg. Nov. 2007;18(6):1264-75. 12 pages.

Kenley et al. Osseous regeneration in the rat calvarium using novel delivery systems for recombinant human bone morphogenetic protein 2 (rhBMP 2). J Biomed Mater Res. Oct. 1994;28(10):1139-47. 9 pages.

Extended European Search Report dated Jul. 19, 2019 issued by the European Patent Office in European Application No. 19158863.1-1109, filed Feb. 22, 2019.

(Continued)

*Primary Examiner* — Susan T Tran
*Assistant Examiner* — William Craigo
(74) *Attorney, Agent, or Firm* — Sorell, Lenna & Schmidt, LLP; William D. Schmidt, Esq.

(57) ABSTRACT

Provided is an injectable implant configured to fit at or near a bone defect to promote bone growth, the injectable implant comprising lyophilized demineralized bone matrix (DBM) being in fiber and particle forms; alginate; and a liquid carrier, wherein the DBM is in an amount of about 20 wt. % to about 40 wt. % of a total weight of the injectable implant, the alginate is in an amount of from about 3 wt. % to about 10 wt. % of the total weight of the injectable implant, and the liquid carrier is in an amount from about 50 wt. % to about 70 wt. % of the total weight of the injectable implant. A moldable implant and methods of making the implants are further provided.

12 Claims, 8 Drawing Sheets

(56) References Cited

OTHER PUBLICATIONS

Qing-Qing Qiu et al: "Effects of e-beam radiation, storage, and hydration on osteoinductivity of DBM/AM composite", Journal of Biomedical Materials Research. Part B: Applied Biomaterials, vol. 91B, No. 1, Oct. 1, 2009 (Oct. 1, 2009), pp. 401-408.
Examination Report issued by the EPO in EP application No. 19158863.1 dated Jun. 25, 2020.

* cited by examiner

| Group | Segments fused (8 wks) |
| --- | --- |
| Injectable – Aseptic | 24/24 |
| Putty – Irradiated | 8/24 |

FIG. 3

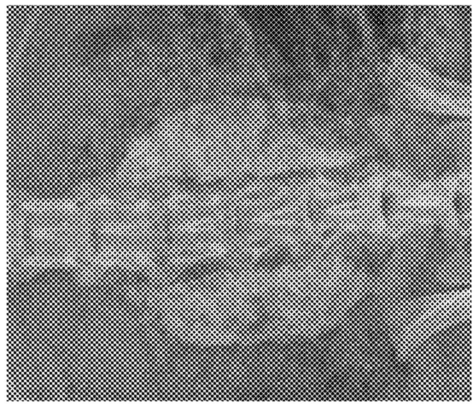
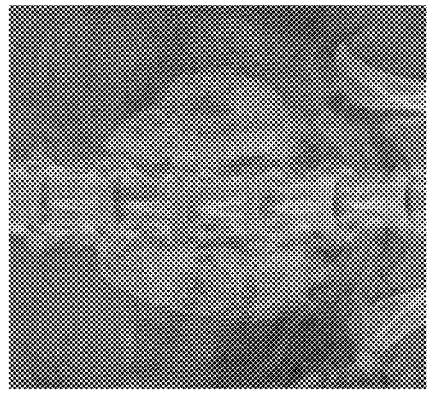
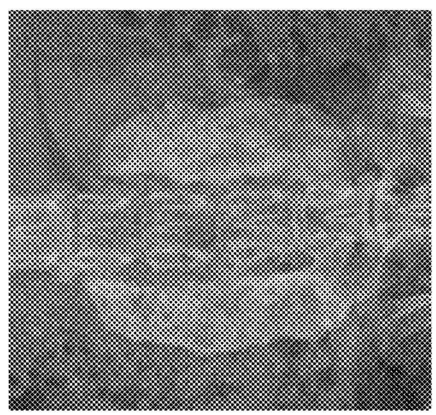
FIG. 4
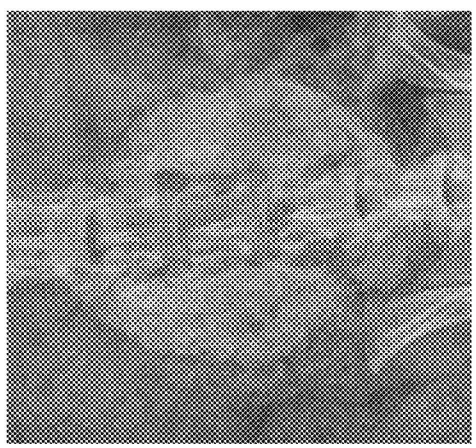

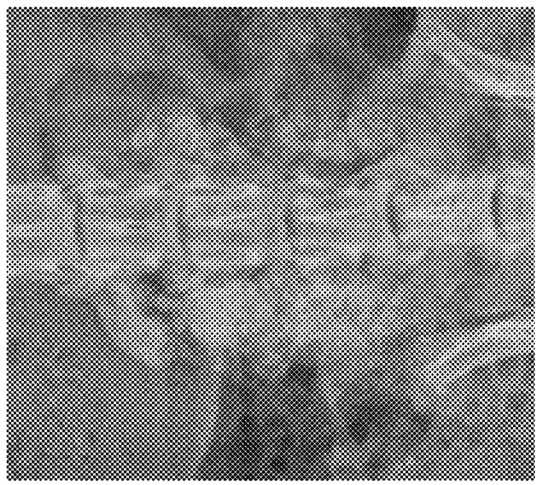
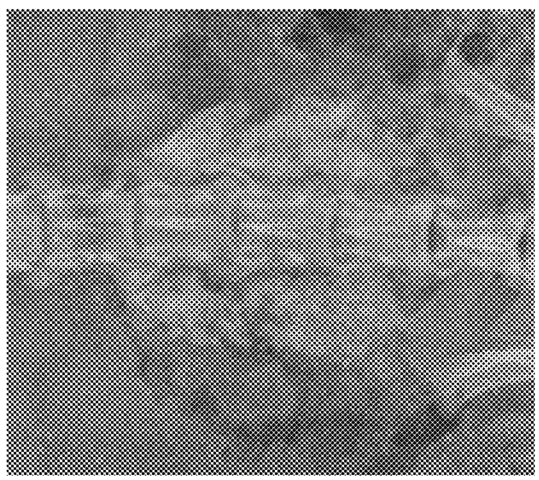
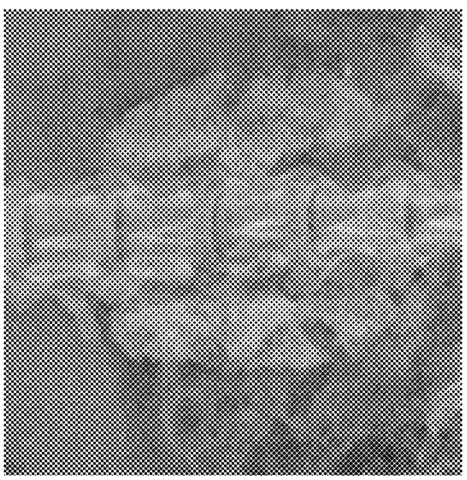
FIG. 5
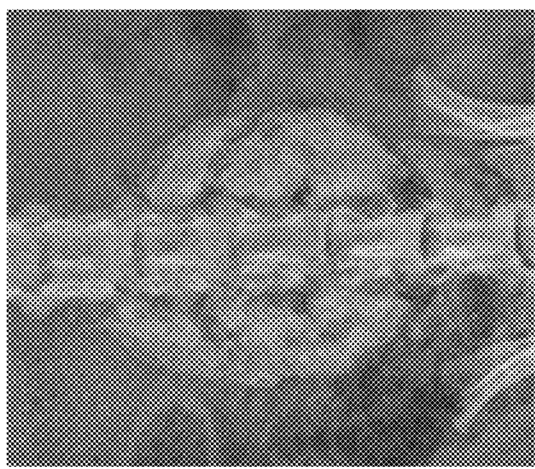
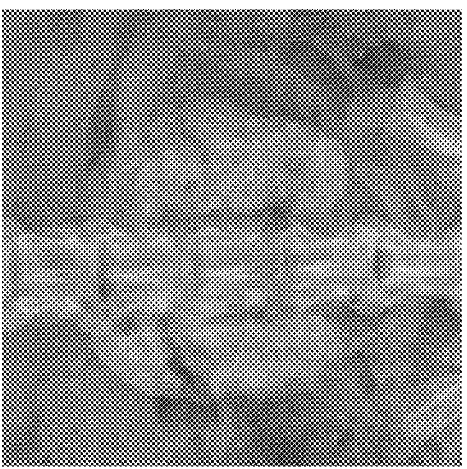

RABBIT PLF

| Group | Rabbits | Description | Bilateral Fusion | Unilateral Fusion |
|---|---|---|---|---|
| 1 | 9 | Putty | 3/6 | 6/12 |
| 2 | 9 | Moldable Implant | 0/6 | 1/12 |
| 3 | 9 | Putty + 50% Autograft | 3/6 | 6/12 |
| 4 | 9 | Moldable Implant + 50% Autograft | 1/6 | 2/12 |
| 5 | 9 | Predicate Irradiated Putty | 0/6 | 0/12 |
| 6 | 9 | Control Autograft | 3/6 | 6/12 |

FIG. 6

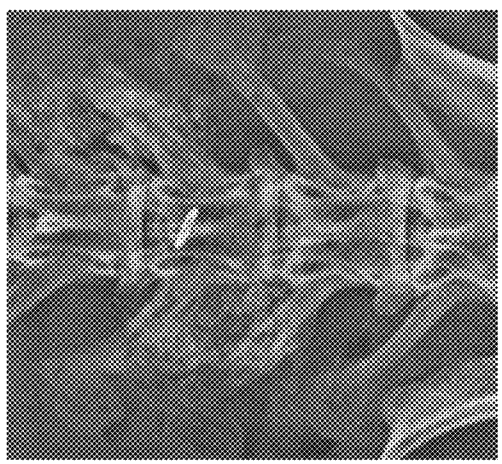
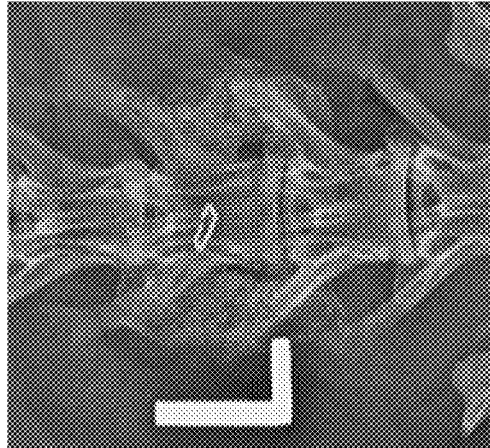
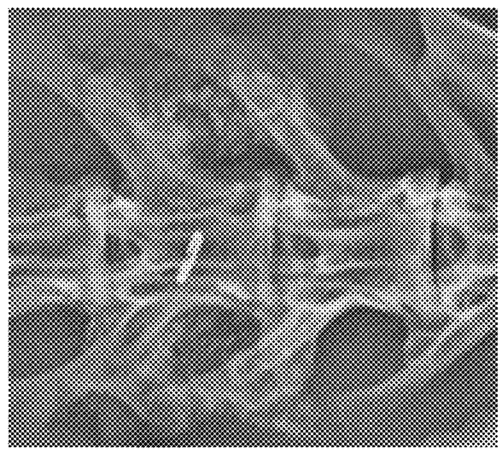
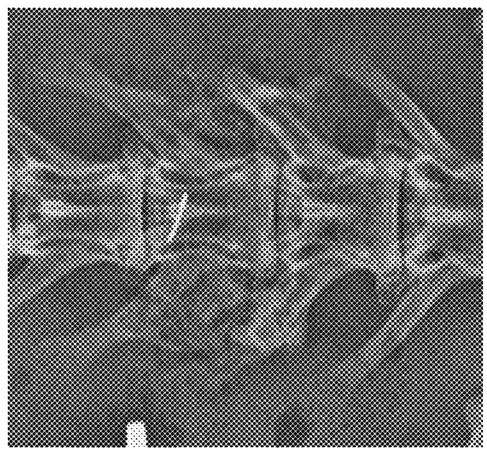
FIG. 7
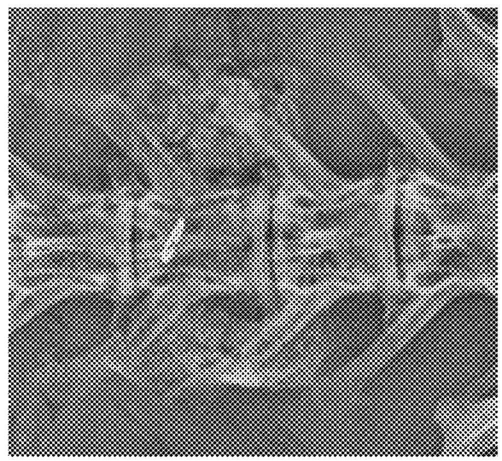
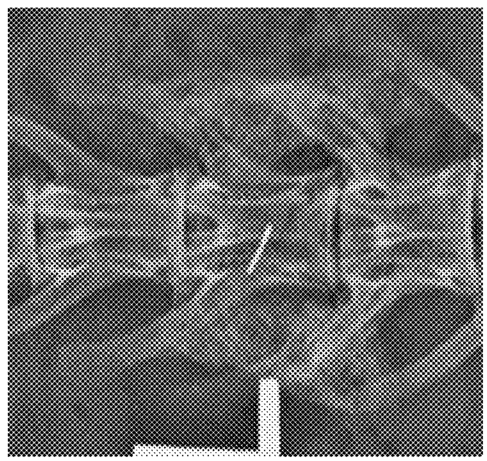

DEMINERALIZED BONE MATRIX HAVING IMPROVED HANDLING CHARACTERISTICS

BACKGROUND

The rapid and effective repair of bone defects caused by injury, disease, wounds, or surgery is a goal of orthopedic surgery. Toward this end, a number of compositions and materials have been used or proposed for use in the repair of bone defects. The biological, physical, and mechanical properties of the compositions and materials are among the major factors influencing their suitability and performance in various orthopedic applications.

Autologous bone ("ACB"), also known as autograft or autogenous bone, is considered the gold standard for bone grafts. Autograft bone is osteoinductive and nonimmunogenic, and, by definition, has all of the appropriate structural and functional characteristics appropriate for the particular recipient. Unfortunately, autograft bone is only available in a limited number of circumstances. Some individuals lack autograft bone of appropriate dimensions and quality for transplantation, and donor site pain and morbidity can pose serious problems for patients and their physicians. Among the known bone repair materials and bone void fillers is autologous cancellous bone. This type of bone has the advantage of being both osteoinductive and nonimmunogenic. Unfortunately, this type of bone is not available under all circumstances.

Moreover, donor site morbidity and trauma add to the limitations of autologous cancellous bone. One alternative to autologous bone is allograft bone. Unfortunately, allograft bone has a lower osteogenic capacity than autograft bone, has a high resorption rate, creates less revascularization at the bone defect site, typically induces a greater immunogenic response and may result in the transfer of certain diseases.

Much effort has been invested in the identification or development of alternative bone graft materials. Demineralized bone matrix ("DBM") implants have been reported to be particularly useful. Demineralized bone matrix is typically derived from cadavers. The bone is removed aseptically and/or treated to kill any infectious agents. The bone is then optionally particulated by milling or grinding. The bone is then treated to remove fats and to extract the mineral components for example, by soaking the bone in an acidic solution.

DBM is a desirable component of bone graft materials because it provides an osteoinductive matrix and exhibits osteoconductive potential, thereby promoting bone growth and healing. DBM is osteoinductive due to the presence of active bone growth factors including bone morphogenetic proteins (BMP). Osteoinductivity depends not only on the concentration of growth factors in DBM, but also on their availability to cells after implantation. Moreover, DBM is fully resorbable, and bone graft materials containing organic DBM are highly biocompatible because it contains many of the components of natural bone. Following implantation, the presence of DBM induces cellular recruitment to the site of injury. The recruited cells may eventually differentiate into bone forming cells. Such recruitment of cells leads to an increase in the rate of wound healing and, therefore, to faster recovery for the patient. Advantageously, DBM costs less than many other available organic bone composition additives, such as isolated bone morphogenetic proteins (BMPs).

One form of administering DBM is by employing solid bone grafts. However, solid bone grafts cannot be effectively manipulated into irregularly shaped bone voids or defects and are at times not ideal for graft placement. DBM putty is therefore beneficial when there is a need to administer a bone graft to irregularly shaped bone voids or defects. Some advantages of using DBM putty is that the putty is moldable and can be easily manipulated into a bone void or defect site. Further, DBM putty can be administered via injection and can be conveniently stored in syringes, thus preventing the DBM putty from drying out and contamination when not in use.

Another component that is often found in bone graft materials since it assists in osteoconduction and osteoinduction of bone is collagen. However, at times, patients can have an adverse reaction to collagen, especially collagen that is derived from a non-human source. For example, an immunogenic reaction can occur in patients when non-human collagen is used. An immunogenic reaction is the ability of a particular substance to provoke an immune response in the body. In other words, it is the ability to induce a humoral and/or cell-mediated immune response.

Further, bone graft materials are commonly irradiated for sterilization purposes. However, sterilization can stripe away natural properties of bone, for example, by denaturing proteins such as natural collagen, which decreases new bone formation via osteoconduction and osteoinduction.

Therefore, there is a need for implantable devices/carriers comprising DBM that are injectable and/or moldable and are configured to fit into many types of bone void defects (e.g., regular or irregular shaped defects). There is also a need for aseptically processed implantable devices/carriers that have enhanced osteoinductivity and osteoconductivity. Accordingly, there is a need for implantable device/carriers that provide high performance and handling characteristics for implantation into a bone void defect.

SUMMARY

An injectable implant is provided that is configured to fit at or near a bone defect to promote bone growth. The injectable implant provides high performance and handling characteristics for implantation into a bone void defect. The injectable implant comprises lyophilized demineralized bone matrix (DBM) being in fiber and particle forms; alginate; and a liquid carrier. The DBM is in an amount of about 20 wt. % to about 40 wt. % of a total weight of the injectable implant, the alginate is in an amount of from about 1 wt. % to about 10 wt. % of the total weight of the injectable implant, and the liquid carrier is in an amount from about 50 wt. % to about 70 wt. % of the total weight of the injectable implant.

In some embodiments, a moldable implant is provided that is configured to fit at or near a bone defect to promote bone growth. The moldable implant comprises lyophilized demineralized bone matrix (DBM) being in fiber, particle and chip forms. The DBM is in an amount of about 15 wt. % to about 40 wt. % based on a total weight of the moldable implant. The moldable implant further comprises an alginate in an amount of from about 3 wt. % to about 20 wt. % based on the total weight of the moldable implant.

In some embodiments, a method of making an injectable or moldable implant is provided, the method comprising mixing lyophilized demineralized bone matrix (DBM) being in fiber and particle forms in an amount of about 28% based on a total weight of the implant, or DBM in fiber, particle and chip forms in an amount of about 30% based on the total weight of the implant with an aqueous liquid comprising an alginate so as to uniformly distribute the DBM within the alginate to form the injectable or moldable implant.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings where:

FIG. 3 is a table of results from a rat two-level posterior lateral fusion (PLF) study where subjects were divided into two groups; group 1, where an injectable aseptic implant was implanted into the subjects at a surgical site and group 2, where an irradiated moldable putty was implanted into the subjects at a surgical site. Results showed that the irradiated moldable putty fused 8 of 24 unilateral segments (33%) while the injectable aseptic implant fused 2.4 of 24 unilateral segments (100%) by manual palpation and radiographically. Further, greater consolidation and organization of new bone was observed radiographically in the aseptic vs. irradiated treatment groups.

FIG. 4 illustrates an x-ray of rat subjects in group 1 that were administered the injectable aseptic implant and their progress at 2 weeks, 4 weeks, and 8 weeks after implantation.

FIG. 5 illustrates an x-ray of rat subjects from group 2 that were administered the irradiated moldable putty and their progress at 2 weeks, 4 weeks, and 8 weeks after implantation, FIG. 6 illustrates a table of results from a rabbit PLF study where subjects were divided into 6 groups; Group 1 contained subjects that were implanted with an injectable putty at a surgical site, Group 2 contained subjects that were implanted with a moldable implant at a surgical site, Group 3 contained subjects that were implanted with a combination product comprising the injectable putty of Group 1 and 50% autograft at a surgical site, Group 4 contained subjects that were implanted with a combination product comprising the moldable implant of Group 2 and 50% autograft at a surgical site, Group 5 contained subjects that were implanted with the predicate irradiated putty at a surgical site, and Group 6 contained subjects that were implanted with the control autograft at a surgical site. Results showed that Group 1 caused bilateral fusion in 3 out of 6 segments and unilateral fusion in 6 out of 12 segments, Group 2 caused bilateral fusion in 0 out of 6 segments and unilateral fusion in 1 out of 12 segments, Group 3 caused bilateral fusion in 3 out of 6 segments and unilateral fusion in 6 out of 12 segments, Group 4 caused bilateral fusion in 1 out of 6 segments and unilateral fusion in 2 out of 12 segments, Group 5 caused bilateral fusion in 0 out of 6 segments and unilateral fusion in 0 out of 12 segments, and Group 6 caused bilateral fusion in 3 out of 6 segments and unilateral fusion in 6 out of 12 segments.

FIG. 7 illustrates an x-ray of rabbit subjects in Group 1 that were administered the injectable putty.

Figure 1:
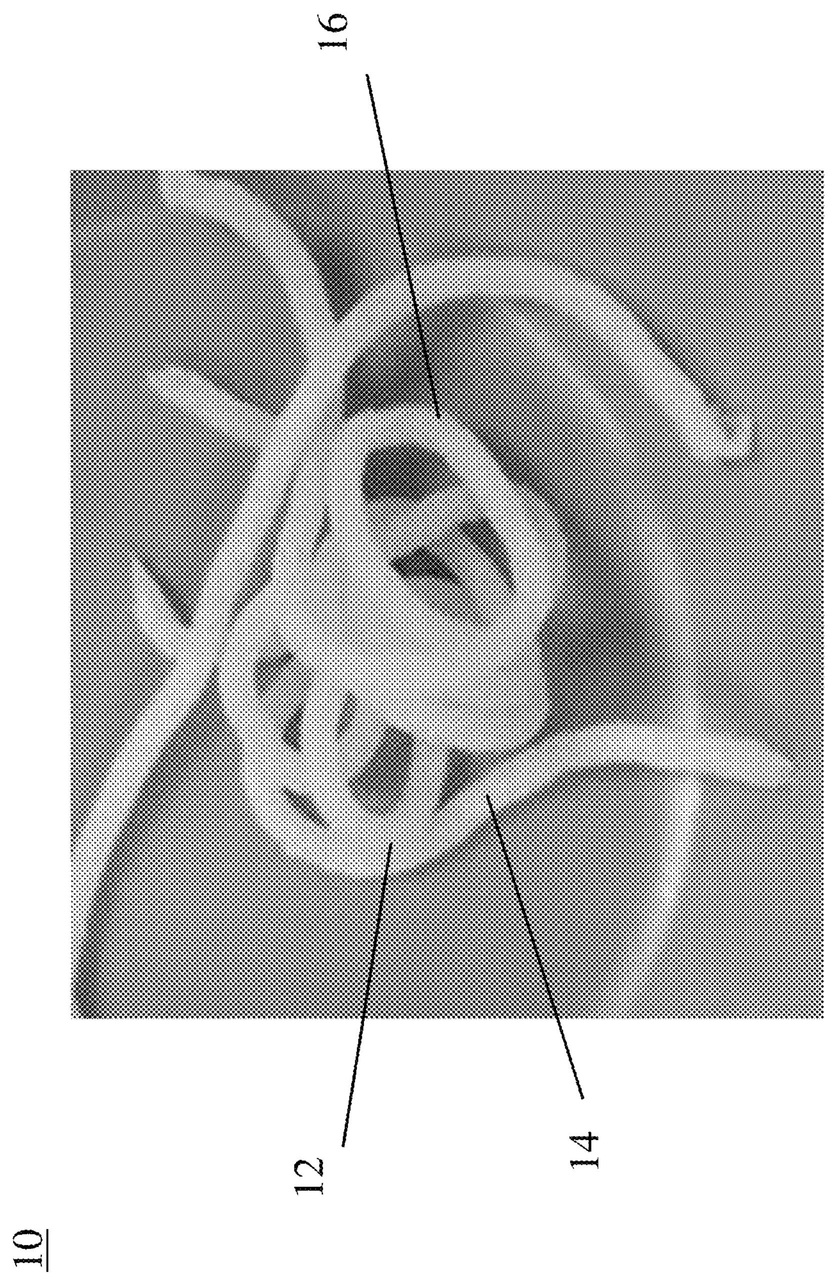
FIG. 1 illustrates an injectable implant configured to increase osteoinductivity and osteoconductivity in bone, the injectable implant comprising DBM fibers, DBM particles, alginate, phosphate buffered saline and sterile filtered water.

It is to be understood that the figures may not be to scale. Further, the relationship between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the present application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub ranges subsumed therein. For example, a range of "1 to 10" includes any and all sub ranges between (and including) the minimum value of 1 and the maximum value of 10, that is, any and all sub ranges having a minimum value of equal to or greater than 1 and a maximum value of equal to or less than 10, e.g., 5.5 to 10.

Definitions

It is noted that, as used in this specification and the appended claims, the singular forms "a," "an," and "the," include plural referents unless expressly and unequivocally limited to one referent. Thus, for example, reference to "an implant" includes one, two, three or more implants.

The term "bioactive agent" as used herein is generally meant to refer to any substance that alters the physiology of a patient. The term "bioactive agent" may be used interchangeably herein with the terms "therapeutic agent," "therapeutically effective amount," and "active pharmaceutical ingredient", "API" or "drug".

Bioactive agent or bioactive compound is used herein to refer to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, prostaglandins, anti-depressants, anti-emetics, and imaging agents. In certain embodiments, the bioactive agent is a drug. Bioactive agents further include RNAs, such as siRNA, and osteoclast stimulating factors. In some embodiments, the bioactive agent may be a factor that stops, removes, or reduces the activity of bone growth inhibitors. In some embodiments, the bioactive agent is a growth factor, cytokine, extracellular matrix molecule or a fragment or derivative thereof, for example, a cell attachment sequence such as RGD. A more complete listing of bioactive agents and specific drugs suitable for use in the present application may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996; and the United States Pharmacopeia-25/National Formulary-20, published by the United States Pharmacopeia Convention, Inc., Rockville Md., 2001, each of which is incorporated herein by reference.

Biocompatible, as used herein, is intended to describe materials that, upon administration in vivo, do not induce undesirable long-term effects.

The term "biodegradable" includes compounds or components that will degrade over time by the action of enzymes, by hydrolytic action and/or by other similar mechanisms in the human body. In various embodiments, "biodegradable" includes that components can break down or degrade within the body to non-toxic components as cells (e.g., bone cells) infiltrate the components and allow repair of the defect. By "bioerodible" it is meant that the compounds or components will erode or degrade over time due, at least in part, to contact with substances found in the surrounding tissue, fluids or by cellular action. By "bioabsorbable" it is meant that the compounds or components will be broken down and absorbed within the human body, for example, by a cell or tissue. "Biocompatible" means that the compounds or components will not cause substantial tissue irritation or necrosis at the target tissue site and/or will not be carcinogenic.

A "therapeutically effective amount" or "effective amount" is such that when administered, the bioactive agent results in alteration of the biological activity, such as, for example, enhancing bone growth, etc. The dosage administered to a patient can be as single or multiple doses depending upon a variety of factors, including the drug's administered pharmacokinetic properties, the route of administration, patient conditions and characteristics (sex, age, body weight, health, size, etc.), and extent of symptoms, concurrent treatments, frequency of treatment and the effect desired. In some embodiments the formulation is designed for immediate release. In other embodiments the formulation is designed for sustained release. In other embodiments, the formulation comprises one or more immediate release surfaces and one or more sustained release surfaces.

A "depot" includes but is not limited to capsules, microspheres, microparticles, microcapsules, microfibers particles, nanospheres, nanoparticles, coating, matrices, wafers, pills, pellets, emulsions, liposomes, micelles, gels, or other pharmaceutical delivery compositions or a combination thereof. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof. In some embodiments, the implant can be a biodegradable depot.

The term "implantable" as utilized herein refers to a biocompatible device (e.g., implant) retaining potential for successful placement within a mammal. The expression "implantable device" and expressions of the like import as utilized herein refers to an object implantable through surgery, injection, or other suitable means whose primary function is achieved either through its physical presence or mechanical properties.

"Localized" delivery includes delivery where one or more implants are deposited within a tissue, for example, a bone cavity, or in close proximity (within about 0.1 cm, or preferably within about 10 cm, for example) thereto.

The term "immunogenic," "immunogenic reaction," or "immunogenicity" refers to the ability of a particular substance, such as an antigen or epitope, to provoke an immune response in the body of a human or animal. In other words, immunogenicity is the ability to induce a humoral and/or cell-mediated immune response. "Unwanted immunogenicity" refers to an immune response by an organism against a therapeutic antigen (e.g., recombinant protein, or monoclonal antibody). This reaction leads to production of anti-drug-antibodies (ADAs) inactivating the therapeutic effects of the treatment and, in rare cases, inducing adverse effects.

The term "mammal" refers to organisms from the taxonomy class "mammalian," including but not limited to humans, other primates such as monkeys, chimpanzees, apes, orangutans and monkeys, rats, mice, rabbits, cats, dogs, pigs, cows, horses, etc.

The term "particle" refers to pieces of DBM bone material having various shapes and sizes that possess regular, irregular or random geometries. In some embodiments. DBM particles include shapes, such as for example, spheres, cubes, cylinders, ovals, granular, or the like. It should be understood that some variation in dimension will occur in the production of the particles and particles demonstrating such variability in dimensions are within the scope of the present application. Particles do not include fibers and chips.

In some embodiments, the implant comprises a matrix. The "matrix" of the present application is utilized as a scaffold for bone and/or cartilage repair, regeneration, and/or augmentation. Typically, the matrix provides a 3-D matrix of interconnecting pores, which acts as a scaffold for cell migration. The morphology of the matrix guides cell migration and cells are able to migrate into or over the matrix, respectively. The cells then are able to proliferate and synthesize new tissue and form bone and/or cartilage. In some embodiments, the matrix can be a putty, paste, cohesive mass, or injectable form.

In some embodiments, the implant can be malleable, cohesive, flowable and/or can be shaped into any shape. The term "malleable" includes that the implant is capable of being converted from a first shape to a second shape by the application of pressure, such as, for example, a putty.

The term "cohesive" as used herein means that the implant tends to remain a singular, connected mass upon movement, including the exhibition of the ability to elongate substantially without breaking upon stretching. An example of a cohesive implant includes, for example, a putty.

The term "moldable" includes that the implant can be shaped by hand or machine or injected in the target tissue site (e.g., bone defect, fracture, or void) into a wide variety of configurations. In some embodiments, the implant can be formed into sheets, blocks, rings, struts, plates, disks, cones, pins, screws, tubes, teeth, bones, portion of bone, wedges, cylinders, threaded cylinders, or the like, as well as more complex geometric configurations.

The term "injectable" refers to a mode of administering the implant. The implant can be administered in a variety of ways such as, for example, a syringe and/or cannula. For example, the implant can be administered parenterally, such as for example, anterior lumbar interbody administration for fusion, or posterior lumbar interbody administration for fusion or transforaminal lumbar interbody administration for fusion, other intraspinal injection or other local administration.

The term "alginate" or "alginates" refer to a type of polysaccharide isolated from brown algae. It is a linear copolymer with homopolymeric blocks of guluronic (G) and mannuronic (M) acids as G monomer blocks, M monomer blocks and guluronic-mannuronic (G-M) alternating sequences. Among these three types of structural elements, only G blocks are involved in the gelation of alginate by reacting with multiple cations such as $Ca^{2+}$ and $Ba^{2+}$.

The monomers can appear in homopolymeric blocks of consecutive G-residues (G-blocks), consecutive M-residues (M-blocks), alternating M and G-residues (G-M blocks) or randomly organized blocks. The relative amount of each block type varies with the origin of the alginate. Alternating blocks form the most flexible chains and are more soluble at lower pH than the other blocks. G-blocks form stiff chain elements, and two G-blocks of more than 6 residues each can form ionically cross-linked junctions with divalent cations e.g. $Ca^{2+}$, $Ba^{2+}$, $Sr^{2-}$ among others, leading to a three-dimensional gel network. In these ionically cross-linked gels, it is mostly the homopolymeric G blocks that form the junctions, where the stability of the gel is determined by the relative amount of divalent cations combined.

There exists a free carboxyl group on each of the plutonic or mannuronic moiety. When these carboxyl groups are not ionized, e.g. in a low pH aqueous environment, alginate molecules are not hydrated and become insoluble. However, alginate molecules become soluble and fully hydrated when the pH is neutral or alkaline. Under this condition, the reaction between G blocks and cations such as $Ca^{2+}$ and $Ba^{2-}$ leads to the ionic gelation of alginate.

In some embodiments, the alginate comprises sodium alginate, potassium alginate, calcium alginate, ammonium alginate, propylene glycol alginate, or a combination thereof.

The term "aseptic", refers to an implant that is free from contamination caused by bacteria, viruses, or other microorganisms.

Bone, as used herein, refers to bone that is cortical, cancellous or cortico-cancellous of autogenous, allogenic, xenogenic, or transgenic origin.

Bone graft, as used herein, refers to any implant prepared in accordance with the embodiments described herein and therefore may include expressions such as bone material and bone membrane.

Demineralized, as used herein, refers to any material generated by removing mineral material from tissue, for example, bone tissue. In certain embodiments, the demineralized compositions described herein include preparations containing less than 5% calcium. In some embodiments, the demineralized compositions may comprise less than 1% calcium by weight. In some embodiments, the compositions may comprise less than 5, 4, 3, 2 and/or 1% calcium by weight. Partially demineralized bone is intended to refer to preparations with greater than 5% calcium by weight but containing less than 100% of the original starting amount of calcium. In some embodiments, partially demineralized bone comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% of the original starting amount of calcium.

In some embodiments, demineralized bone has less than 95% of its original mineral content. In some embodiments, demineralized bone less than 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6 and/or 5% of its original content. In some embodiments, "Demineralized" is intended to encompass such expressions as "substantially demineralized," "partially demineralized," "surface demineralized," and "fully demineralized." "Partially demineralized" is intended to encompass "surface demineralized."

In some embodiments, the demineralized bone may be surface demineralized from about 1-99%. In some embodiments, the demineralized bone is 1, 2, 3, 4, 5, 6, 7, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% surface demineralized. In various embodiments, the demineralized bone may be surface demineralized from about 15-25%. In some embodiments, the demineralized bone is 15, 16, 17, 18, 19, 20, 21, 22, 23, 24 and/or 25% surface demineralized.

Demineralized bone matrix (DBM), as used herein, refers to any material generated by removing mineral material from bone tissue. In some embodiments, the DBM compositions as used herein include preparations containing less than 5% calcium and, in some embodiments, less than 1% calcium by weight. In some embodiments, the DBM compositions include preparations that contain less than 5, 4, 3, 2 and/or 1% calcium by weight. In other embodiments, the DBM compositions comprise partially demineralized bone (e.g., preparations with greater than 5% calcium by weight but containing less than 100% of the original starting amount of calcium).

In some embodiments, part or all of the surface of the bone can be demineralized. For example, part or all of the surface of the bone material can be demineralized to a depth of from about 100 to about 5000 microns, or about 150 microns to about 1000 microns. In some embodiments, part or all of the surface of the bone material can be demineralized to a depth of from about 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950 to about 5000 microns. If desired, the implant can comprise demineralized material.

Osteoconductive, as used herein, refers to the ability of a substance to serve as a template or substance along which bone may grow.

Osteogenic, as used herein, refers to materials containing living cells capable of differentiation into bone tissue.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference.

Superficially demineralized, as used herein, refers to bone-derived elements possessing at least about 90 weight percent of their original inorganic mineral content. In some embodiments, superficially demineralized contains at least about 90, 91, 92, 93, 94, 95, 96, 97, 98 and/or 99 weight percent of their original inorganic material. The expression "partially demineralized" as used herein refers to bone-derived elements possessing from about 8 to about 90 weight percent of their original inorganic mineral content. In some embodiments, partially demineralized contains about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 and/or 90 weight percent of their original inorganic mineral content. The expression "fully demineralized" as used herein refers to bone containing less than 8% of its original mineral context. In some embodiments, fully demineralized contains about less than 8, 7, 6, 5, 4, 3, 2 and/or 1% of its original mineral content.

The expression "average length to average thickness ratio" as applied to the DBM fibers of the present application means the ratio of the longest average dimension of the fiber (average length) to its shortest average dimension (average thickness). This is also referred to as the "aspect ratio" of the fiber.

Fibrous, as used herein, refers to bone elements whose average length to average thickness ratio or aspect ratio of the fiber is from about 50:1 to about 1000:1. In some embodiments, average length to average thickness ratio or aspect ratio of the fiber is from about 50:1, 75:1, 100:1, 125:1, 150:1, 175:1, 200:1, 225:1, 250:1, 275:1, 300:1, 325:1, 350:1, 375:1, 400:1, 425:1, 450:1, 475:1, 500:1, 525:1, 550:1, 575:1, 600:1, 625:1, 650:1, 675:1, 700:1, 725:1, 750:1, 775:1, 800:1, 825:1, 850:1, 875:1, 900:1, 925:1, 950:1, 975:1 to about 1000:1. In overall appearance the fibrous bone elements can be described as bone fibers, threads, narrow strips, or thin sheets. Often, where thin sheets are produced, their edges tend to curl up toward each other. The fibrous bone elements can be substantially linear in appearance or they can be coiled to resemble springs. In some embodiments, the bone fibers are of irregular shapes including, for example, linear, serpentine or curved shapes. The bone fibers are preferably demineralized however some of the original mineral content may be retained when desirable for a particular embodiment. In various embodiments, the bone fibers are mineralized. In some embodiments, the fibers are a combination of demineralized and mineralized.

Non-fibrous, as used herein, refers to elements that have an average width substantially larger than the average thickness of the fibrous bone element or aspect ratio of less than from about 50:1 to about 1000:1. Preferably the non-fibrous bone elements are shaped in a substantially regular manner or specific configuration, for example, triangular prism, sphere, cube, cylinder and other regular shapes. By contrast, particles such as chips, shards, or powders possess irregular or random geometries. It should be understood that some variation in dimension will occur in the production of the elements of this application and elements demonstrating such variability in dimension are within the scope of this application and are intended to be understood herein as being within the boundaries established by the expressions "mostly irregular" and "mostly regular".

"Surface demineralized fibrous bone chip," as used herein, refers to surface demineralized bone chip(s) that have been subjected to mild pressure from about 5,000, 5,500, 6,000, 6,500, 7,000, 7,500, 8,000, 8,500, 9,000, 9,500, to about 10,000 pounds per square inch (psi).

The section headings below should not be restricted and can be interchanged with other section headings.

Implantable Device

In some embodiments, an injectable implant 10 is provided that is configured to fit at or near a bone defect to promote bone growth, as shown in FIG. 1. In some embodiments, the injectable implant is administered via a syringe and/or a cannula. In some embodiments, the bone defect is a bone void. The injectable implant is configured to be a bone void filler that is injectable in a putty form. The injectable implant comprises lyophilized demineralized bone matrix (DBM) 12 in fiber and particle forms, alginate 14, and a liquid carrier such as phosphate buffered saline (PBS) 16. The injectable implant shown in 10 has a combination of DBM fibers and DBM particles that are uniformly distributed throughout the alginate. The injectable implant also does not contain collagen so that an immunogenic reaction does not occur in patients that are administered the injectable implant.

The injectable implant is aseptically processed to enhance osteoinductivity and osteoconductivity of bone. Aseptically processing techniques as described below, prevent natural properties of bone from being striped, thus increasing the production of new bone formation via osteoconduction and osteoinduction.

In some embodiments, the DBM is fully demineralized. In some embodiments, the fully demineralized DBM contains about less than 8, 7, 6, 5, 4, 3, 2 and/or 1% of its original mineral content. In some embodiments, the DBM is partially demineralized, surface demineralized and/or fully demineralized.

In some embodiments, the DBM is in both fiber and particle forms. In some embodiments, the fibers have a size of from about 1 to about 7 mm. In some embodiments, the fibers have a size from about 1 to about 20 mm, from about 1 to about 15 mm, from about 1 to about 10 mm, from about 2 to about 15 mm, from about 2 to about 10 mm, from about 2 to about 5 mm, from about 3 to about 15 mm, from about 3 to about 10 mm, from about 1 to about 5 mm, from about 4 to about 15 mm, from about 10 mm, from about 4 to about 5 mm, from about 5 to about 15 mm, or from about 5 to about 10 mm. In some embodiments, the fibers have a size from about 1 to about 50 mm, from about 5 to about 40 mm, from about 5 to about 30 mm, from about 5 to about 10 mm. In some embodiments, the fibers have a size of from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 to about 50 mm.

In some embodiments, the particles have a size of from about 100 microns to about 1000 microns. In some embodiments, the particles have a size of from about 100 microns to about 500 microns, from about 100 microns to about 250 microns, from about 200 microns to about 1000 microns, from about 200 microns to about 800 microns, from about 200 microns to about 600 microns, from about 200 microns to about 400 microns, from about 200 microns to about 300 microns, from about 300 microns to about 800 microns, from about 300 microns to about 600 microns, from about 300 microns to about 400 microns, from about 400 microns to about 1000 microns, from about 400 microns to about 600 microns, from about 500 microns to about 1000 microns, from about 500 microns to about 800 microns, from about 500 microns to about 600 microns.

In some embodiments, the particles have a size of from about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995 to about 1000 microns.

In some embodiments, the DBM is in an amount of about 20 wt. % to about 40 wt. % of a total weight of the injectable implant. In some embodiments, the DBM is in an amount of from about 20, 21, 22, 23, 24, 25, 26, 27, 28, 29, 30, 31, 32, 33, 34, 35, 36, 37, 38, 39, to about 40 wt. % of the total weight of the implant. In some embodiments, the DBM is in an amount of about 1 to about 99 wt. % of the total weight of the implant. In some embodiments, the DBM is in an amount of from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 88, 89, 90, 91, 92, 93, 94, 95, 96, 97, 98, to about 99 wt. % of the total weight of the implant.

In some embodiments, the injectable implant comprises a ratio of fiber and particle forms of about 50:50. In some embodiments, the injectable implant comprises a ratio of fibers and particle forms of from about 50:1, 1:50, 25:1, 1:25, 75:25, 25:75, 1:12, 12:1, 1:10, 10:1, 8:1, 1:8, 6:1, 1:6, 5:1, 1:5, or 4:1 to about 1:4.

In some embodiments, from about 1, 2, 3, 4, 5, 6, 7, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, to about 99% of the DBM comprises the fiber form (e.g., fibers) In some embodiments, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 of the DBM comprises the particle form (e.g., particles).

In some embodiments, the alginate is in an amount of from about 1 wt. % to about 10 wt. % of the total weight of the injectable implant. In some embodiments, the alginate is in an amount of from about 3 to about 8 wt. %, of from about 5 to about 7 wt. % or of from about 4 to 6 wt. % of the total weight of the injectable implant. In some embodiments, the alginate is in an amount of from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, to about 99 wt. % of the total weight of the implant.

In some embodiments, the alginate is a sterile sodium alginate. In some embodiments, the alginate is sodium alginate, potassium alginate, calcium alginate, ammonium alginate, propylene glycol alginate, or a combination thereof.

In some embodiments, the alginate is in a powder form and has a particle size of from about 100 to about 1,000 microns. In some embodiments, the particle size of the alginate is of from about 100 microns to about 500 microns, from about 100 microns to about 250 microns, from about 200 microns to about 1000 microns, from about 200 microns to about 800 microns, from about 200 microns to about 600 microns, from about 200 microns to about 400 microns, from about 200 microns to about 300 microns, from about 300 microns to about 800 microns, from about 300 microns to about 600 microns, from about 300 microns to about 400 microns, from about 400 microns to about 1000 microns, from about 400 microns to about 600 microns, from about 500 microns to about 1000 microns, from about 500 microns to about 800 microns, from about 500 microns to about 600 microns.

In some embodiments, the alginate powder has a particle size of from about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995 to about 1000 microns.

In some embodiments, the alginate has an average molecular weight of about 100,000 to about 600,000 Daltons (Da). In some embodiments, the alginate has an average molecular weight of from about 100,000 to about 500,000 Da, or of from about 200,000 to about 400,000 Da. In some embodiments, the alginate has an average molecular weight of from about 200,000, 225,000, 250,000, 275,000, 300,000, 325,000, 350,000, 375,000, 400,000, 425,000, 450,000, 475, 000, 500,000 525,000, 550,000, 575,000 or about 600,000 Da.

In some embodiments, when the alginate powder is mixed in a solution, such as the phosphate buffered saline, the alginate comprises a viscosity of about 20 to about 2,000 centipoises (cps). In some embodiments, the alginate comprises a viscosity of from about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, 1510, 1520, 1530, 1540, 1550, 1560, 1570, 1580, 1590, 1600, 1610, 1620, 1630, 1640, 1650, 1660, 1670, 1680, 1690, 1700, 1710, 1720, 1730, 1740, 1750, 1760, 1770, 1780, 1790, 1800, 1810, 1820, 1830, 1840, 1850, 1860, 1870, 1880, 1890, 1900, 1910, 1920, 1930, 1940, 1950, 1960, 1970, 1980, 1990 to about 2000 cps.

In some embodiments, the phosphate buffered saline is in an amount from about 50 wt. % to about 70 wt. % of the total weight of the injectable implant. In some embodiments, the phosphate buffered saline is in an amount of from about 55 wt. % to about 65 wt. %, or from about 60 wt. % to about 70 wt. % of the total weight of the injectable implant. In some embodiments, the phosphate buffered saline is in an amount of 50, 51, 52, 53, 54, 55, 56, 57, 58, 59, 60, 61, 62, 63, 64, 65, 66, 67, 68, 69, or 70 wt. % of the total weight of the injectable implant.

In one embodiment, the DBM is in an amount of about 28 wt. % based on the total weight of the injectable implant, the alginate is in an amount of about 6 wt. % based on the total weight of the injectable implant, and the phosphate buffered saline is in an amount of about 66 wt. % based on the total weight of the injectable implant.

The injectable implant further comprises sterile water. In some embodiments, the sterile water is in an amount of about 1 to about 50 wt. % based on the total weight of the injectable implant. In some embodiments, the sterile water is in an amount of from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, to about 50 wt. % based on the total weight of the injectable implant.

In various embodiments, the injectable implant has an inherent viscosity (IV) of from about 0.1 dL/g to about 1.2 dL/g or from about 0.20 dL/g to about 0.50 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.55 dL/g, about 0.50 to about 0.70 dL/g, about 0.55 to about 0.6 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, or about 1.8 to about 2.1 dL/g.

In some embodiments, the injectable implant may have a pre-dosed viscosity in the range of about 1 to about 3000 centipoise (cps), 1 to about 2000 cps, 1 to about 1500 cps, 1 to about 1000 cps. 1 to about 500 cps, 1 to about 300 cps, or 1 to about 100 cps. In some embodiments, the injectable implant may have a pre-dosed viscosity of from about 1, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, to about 3000 cps.

In some embodiments, a viscosity enhancing agent is added to the injectable implant in an amount from about 0.1 to about 20 wt. % of the total weight of the injectable implant. In some embodiments, a viscosity enhancing agent is added to the injectable implant in an amount of from about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19 to about 20 wt. % of the total weight of the injectable implant. In some embodiments, the viscosity enhancing agent comprises mannitol, trehalose, hydroxypropyl cellulose, hydroxypropyl methylcellulose, hydroxyethyl methylcellulose, carboxymethylcellulose and salts thereof, Carbopol, poly-(hydroxyethyl-methacrylate), poly-(methoxyethylmethacrylate), poly (methoxyethoxyethylmethacrylate), polymethylmethacrylate (PMMA), methylmethacrylate (MMA), gelatin, polyvinyl alcohols, propylene glycol, mPEG, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In some embodiments, the injectable implant has a modulus of elasticity in the range of 150 to about 2200 Pascals (Pa). In some embodiments, the injectable implant has a modulus of elasticity in the range of 150 to about 300, from about 150 to about 500, from about 150 to about 800, from about 150 to about 1000, from about 150 to about 1300, from about 150 to about 1500, from about 150 to about 1800, from about 150 to about 2000, from about 500 to about 1000, from about 500 to about 1300, from about 500 to about 1500, from about 500 to about 1800, from about 500 to about 2000, from about 500 to about 2200, from about 1000 to about 1300, from about 1000 to about 1500, from about 1000 to about 1800, from about 1000 to about 2000, from about 1000 to about 2200, from about 1300 to about 1500, from about 1300 to about 1800, from about 1300 to about 2000, from about 1300 to about 2200, from about 1500 to about 1800, from about 1500 to about 2000, from about 1500 to about 2200, from about 1800 to about 2000, from about 1800 to about 2200, from about 2000 to about 2200 Pa.

In some embodiments, the injectable implant has a density of between about 2 g/cm$^3$, and about 0.01 g/cm$^3$. In some embodiments, the injectable implant has a density of between about 1.5 g/cm$^3$, and about 0.05 g/cm$^3$. For example, the density may be less than about 2 g/cm$^3$, 1.5 g/cm$^3$, 1 g/cm$^3$, less than about 0.7 g/cm$^3$, less than about 0.6 g/cm$^3$, less than about 0.5 g/cm$^3$, less than about 0.4 g/cm$^3$, less than about 0.3 g/cm$^3$, less than about 0.2 g/cm$^3$, or less than about 0.1 g/cm$^3$.

In some embodiments, if the injectable implant is to be placed in the spinal area, then the injectable implant can comprise preservative free material.

Figure 2:
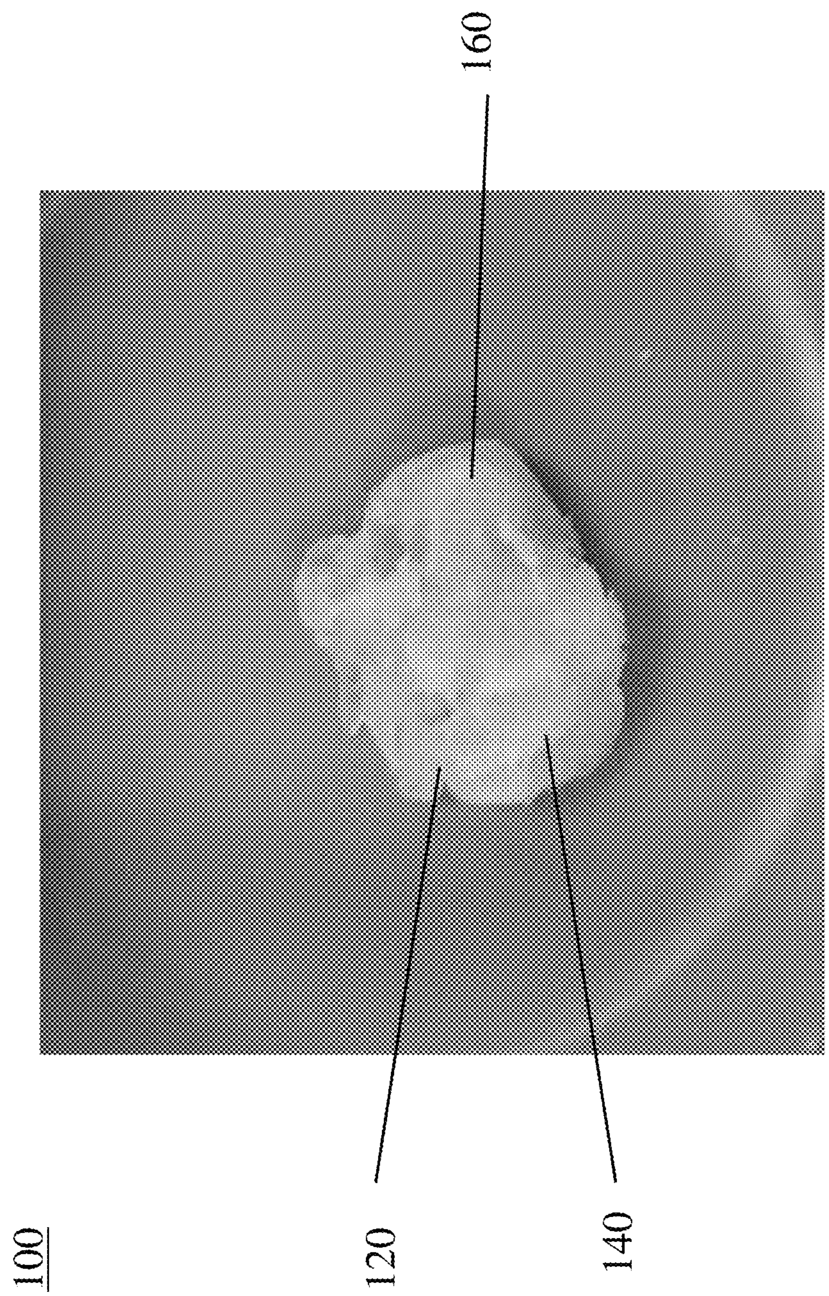
FIG. 2 illustrates a moldable implant configured to increase osteoinductivity and osteoconductivity in bone, the moldable implant comprising DBM fibers, DBM particles, DBM chips, alginate, phosphate buffered saline, and sterile filtered water.

In some embodiments, a moldable implant 100 is provided that is configured to fit at or near a bone defect to promote bone growth, as shown in FIG. 2. In some embodiments, the bone defect is a bone void and the moldable implant is configured to be a bone void filler. In some embodiments, the moldable implant is a putty. The moldable implant is configured to be moldable to any desired shape to fit the bone defect site. The shape of the moldable implant may be tailored to the site at which it is to be situated.

In some embodiments, a medical practitioner may mold the moldable implant into a desired shape and allow the moldable implant to cure or dry prior to implantation. In some embodiments, the moldable implant is malleable in vivo. In such embodiments, a medical practitioner may mold the implant directly into a bone defect site. The moldable implant is malleable and configured to be pressed into a bone defect site to fill out crevices in a bone defect site. In some embodiments, the moldable implant is malleable when wetted and is configured to remain malleable while in contact with the bone defect site. In some embodiments, the moldable implant can be formed to fit into the void space of an interbody cage or around the outside of the cage in the intervertebral space.

The moldable implant comprises lyophilized DBM 120 being in fiber, particle and chip forms, and an alginate 140. In the embodiment shown, the DBM fibers, DBM particles and DBM chips are uniformly distributed throughout the alginate. The alginate holds the DBM fibers, DBM particles and DBM chips together to form a cohesive moldable implant. The moldable implant also does not contain collagen so that an immunogenic reaction does not occur in patients that are administered the moldable implant.

The moldable implant is aseptically processed to enhance osteoinductivity and osteoconductivity of bone. Aseptically processing techniques as described below, prevent natural properties of bone from being striped, thus increasing the production of new bone formation via osteoconduction and osteoinduction.

In some embodiments, the DBM is fully demineralized. In some embodiments, the fully demineralized DBM contains about less than 8, 7, 6, 5, 4, 3, 2 and/or 1% of its original mineral content. In some embodiments, the DBM is partially demineralized, surface demineralized and/or fully demineralized as mentioned above.

In some embodiments, the DBM is in fiber, particle and chip forms. In some embodiments, the DBM fibers have a size of from about 1 to about 7 mm. In some embodiments, the fibers have a size from about 1 to about 20 mm, from about 1 to about 15 mm, from about 1 to about 10 mm, from about 2 to about 15 mm, from about 2 to about 10 mm, from about 2 to about 5 mm, from about 3 to about 15 mm, from about 3 to about 10 mm, from about 1 to about 5 mm, from about 4 to about 15 mm, from about 10 mm, from about 4 to about 5 mm, from about 5 to about 15 mm, or from about 5 to about 10 mm. In some embodiments, the fibers have a size from about 1 to about 50 mm, from about 5 to about 40 mm, from about 5 to about 30 mm, from about 5 to about 10 mm. In some embodiments, the fibers have a size of from about 1, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 to about 50 mm.

In some embodiments, the DBM particles have a size of from about 100 microns to about 1000 microns. In some embodiments, the particles have a size of from about 100 microns to about 500 microns, from about 100 microns to about 250 microns, from about 200 microns to about 1000 microns, from about 200 microns to about 800 microns, from about 200 microns to about 600 microns, from about 200 microns to about 400 microns, from about 200 microns to about 300 microns, from about 300 microns to about 800 microns, from about 300 microns to about 600 microns, from about 300 microns to about 400 microns, from about 400 microns to about 1000 microns, from about 400 microns to about 600 microns, from about 500 microns to about 1000 microns, from about 500 microns to about 800 microns, from about 500 microns to about 600 microns.

In some embodiments, the DBM particles have a size from about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995 to about 1000 microns.

In some embodiments, the DBM chips have a size range of from about 1 to about 4 mm. In some embodiments, the chips have a size range of from about 0.1 to about 50 mm, from about 0.1 to about 30 mm, from about 0.5 to about 20 mm, from about 1 to about 40 mm, from about 1 to about 30 mm, from about 1 to about 20 mm, from about 1 to about 15 mm, from about 1 to about 10 mm, from about 1 to about 5 mm, from about 1 to about 3 mm, from about 1 to about 2 mm, from about 2 to about 15 mm, from about 2 to about 10 mm, from about 2 to about 5 mm, from about 3 to about 15 mm, from about 3 to about 10 mm, from about 4 to about 15 mm, from about 4 to about 5 mm, from about 5 to about 15 mm, or from about 5 to about 10 mm.

In some embodiments, the DBM chips have a size of from about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 to about 50 mm.

In some embodiments, the DBM is in an amount of about 15 wt. % to about 40 wt. % based on a total weight of the moldable implant. In some embodiments, the DBM is in an amount of from about 15, 16, 17, 18, 19, 20, 21, 22, 23, 24, 25, 26, 27, 28, 29, 30, 31, 32, 33, 34, 35, 36, 37, 38, 39, to about 40 wt. % of the total weight of the implant. In some embodiments, the DBM is in an amount of about 1 to about 99 wt. % of the total weight of the implant. In some embodiments, the DBM is in an amount of from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, to about 99 wt. % of the total weight of the implant.

In some embodiments, the moldable implant comprises a ratio of fiber, particle and chip forms of about 33:33:33. In some embodiments, the moldable implant comprises a ratio of fiber, particle and chip forms of from about 1:2:1, 2:1:1, 1:2:2, 1:3:1, 3:1:1, 1:3:3, 1:4:1, 4:1:1, 1:4:4, 1:5:1, 5:1:1, 1:5:5, 1:6:1, 6:1:1, 1:1:6, 1:7:1, 7:1:1, 1:1:7, 1:8:1, 8:1:1, 1:1:8, 1:9:1, 9:1:1, 1:1:9, 1:10:1, 10:1:1 to about 1:1:10.

In some embodiments, from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 to about 99% of the DBM comprises the fiber form (e.g., fibers). In some embodiments, from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 to about 99% of the DBM comprises the particle form (e.g., particles). In some embodiments, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, to about 99% of the DBM comprises the chip form (e.g., chips).

The alginate holds the DBM particles, DBM fiber, and/or the DBM chips together in the injectable putty or moldable implant. In some embodiments, the alginate is in an amount of from about 3 wt. % to about 20 wt. % based on the total weight of the moldable implant. In some embodiments, the alginate is in an amount of from about 5 to about 15 wt. %, of from about 10 to about 20 wt. % or of from about 1 to 5 wt. % of the total weight of the moldable implant. In some embodiments, the alginate is in an amount of from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, to about 99 wt. % of the total weight of the implant.

In some embodiments, the alginate is a sterile sodium alginate. In some embodiments, the alginate is sodium alginate, potassium alginate, calcium alginate, ammonium alginate, propylene glycol alginate, or a combination thereof.

In some embodiments, the alginate is in a powder form and has a particle size of from about 100 to about 1,000 microns. In some embodiments, the particle size of the alginate is of from about 100 microns to about 500 microns, from about 100 microns to about 250 microns, from about 200 microns to about 1000 microns, from about 200 microns to about 800 microns, from about 200 microns to about 600 microns, from about 200 microns to about 400 microns, from about 200 microns to about 300 microns, from about 300 microns to about 800 microns, from about 300 microns to about 600 microns, from about 300 microns to about 400 microns, from about 400 microns to about 1000 microns, from about 400 microns to about 600 microns, from about 500 microns to about 1000 microns, from about 500 microns to about 800 microns, from about 500 microns to about 600 microns.

In some embodiments, the alginate powder has a particle size of from about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995 to about 1000 microns.

In some embodiments, the alginate has an average molecular weight of about 100,000 to about 600,000 Daltons (Da). In some embodiments, the alginate has an average molecular weight of from about 100,000 to about 500,000 Da, or of from about 200,000 to about 400,000 Da. In some embodiments, the alginate has an average molecular weight of from about 200,000, 225,000, 250,000, 275,000, 300,000, 325,000, 350,000, 375,000, 400,000, 425,000, 450,000, 475,000, 500,000, 525,000, 550,000, 575,000 to about 600,000 Da.

In some embodiments, when the alginate powder is mixed in an aqueous carrier, such as phosphate buffered saline, the alginate comprises a viscosity of about 20 to about 2,000 centipoises (cps). In some embodiments, the alginate comprises a viscosity of from about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, 1510, 1520, 1530, 1540, 1550, 1560, 1570, 1580, 1590, 1600, 1610, 1620, 1630, 1640, 1650, 1660, 1670, 1680, 1690, 1700, 1710, 1720, 1730, 1740, 1750, 1760, 1770, 1780, 1790, 1800, 1810, 1820, 1830, 1840, 1850, 1860, 1870, 1880, 1890, 1900, 1910, 1920, 1930, 1940, 1950, 1960, 1970, 1980, 1990 to about 2000 cps.

The moldable implant further comprises an aqueous carrier comprising phosphate buffered saline 160. The aqueous carrier is uniformly distributed throughout the implant and is used to allow a uniformly mixed implant.

The phosphate buffered saline is in an amount from about 40 wt. % to about 60 wt. % based on the total weight of the moldable implant. In some embodiments, the phosphate buffered saline is in an amount of from about 40 wt. % to about 50 wt. % or from about 50 wt. % to about 60 wt. % of the total weight of the moldable implant. In some embodiments, the phosphate buffered saline is in an amount of from about 40, 41, 42, 43, 44, 45, 46, 47, 48, 49, 50, 51, 52, 53, 54, 55, 56, 57, 58, 59, to about 60 wt. % of the total weight of the moldable implant.

In one embodiment, the DBM is in an amount of about 30 wt. % based on the total weight of the moldable implant, the alginate is in an amount of about 14 wt. % based on the total weight of the moldable implant, and the phosphate buffered saline is in an amount of about 54 wt. % based on the total weight of the moldable implant.

The moldable implant further comprises sterile water. In some embodiments, the sterile water is in an amount of about 1 to about 50 wt. % based on the total weight of the moldable implant. In some embodiments, the sterile water is in an amount of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, to about 50 wt. % based on the total weight of the moldable implant.

In various embodiments, the moldable implant has an inherent viscosity (IV) of from about 0.10 dL/g to about 1.2 dL/g or from about 0.20 dL/g to about 0.50 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.55 dL/g, about 0.50 to about 0.70 dL/g, about 0.55 to about 0.6 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, or about 1.8 to about 2.1 dL/g.

In some embodiments, a viscosity enhancing agent is added to the moldable implant in an amount from about 0.1 to about 20 wt. % of the total weight of the moldable implant. In some embodiments, a viscosity enhancing agent is added to the moldable implant in an amount of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19 or about 20 wt. % of the total weight of the moldable implant. In some embodiments, the viscosity enhancing agent comprises mannitol, trehalose, hydroxypropyl cellulose, hydroxypropyl methylcellulose, hydroxyethyl methylcellulose, carboxymethylcellulose and salts thereof, Carbopol, poly-(hydroxyethylmethacrylate), poly-(methoxyethylmethacrylate), poly (methoxyethoxyethylmethacrylate), polymethylmethacrylate (PMMA), methylmethacrylate (MMA), gelatin, polyvinyl alcohols, propylene glycol, mPEG, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In some embodiments, the moldable implant has a modulus of elasticity in the range of 150 to about 2200 Pascals (Pa). In some embodiments, the moldable implant has a modulus of elasticity in the range of 150 to about 300, from about 150 to about 500, from about 150 to about 800, from about 150 to about 1000, from about 150 to about 1300, from about 150 to about 1500, from about 150 to about 1800, from about 150 to about 2000, from about 500 to about 1000, from about 500 to about 1300, from about 500 to about 1500, from about 500 to about 1800, from about 500 to about 2000, from about 500 to about 2200, from about 1000 to about 1300, from about 1000 to about 1500, from about 1000 to about 1800, from about 1000 to about 2000, from about 1000 to about 2200, from about 1300 to about 1500, from about 1300 to about 1800, from about 1300 to about 2000, from about 1300 to about 2200, from about 1500 to about 1800, from about 1500 to about 2000, from about 1500 to about 2200, from about 1800 to about 2000, from about 1800 to about 2200, from about 2000 to about 2200 Pa.

In some embodiments, the moldable implant has a density of between about 2 g/cm$^3$, and about 0.01 g/cm$^3$. In some embodiments, the moldable implant has a density of between about 1.5 g/cm$^3$, and about 0.05 g/cm$^3$. For example, the density may be less than about 2 g/cm$^3$, 1.5 g/cm$^3$, 1 g/cm$^3$, less than about 0.7 g/cm$^3$, less than about 0.6 g/cm$^3$, less than about 0.5 g/cm$^3$, less than about 0.4 g/cm$^3$, less than about 0.3 g/cm$^3$, less than about 0.2 g/cm$^3$, or less than about 0.1 g/cm$^3$.

In some embodiments, if the moldable implant is to be placed in the spinal area, then the moldable implant will comprise preservative free material.

In some embodiments, the aqueous carrier comprising phosphate buffered saline can alternatively or further include a variety of additional fluids. In some embodiments, the aqueous carrier comprises phosphate buffered saline, sterile water, physiological saline, sodium chloride, dextrose, Lactated Ringer's solution, or a combination thereof.

In some embodiments, the injectable implant and/or the moldable implant further comprises hyaluronic acid, cellulose ethers (such as carboxymethylcellulose), collagen, gelatin, autoclaved bone powder, osteoconductive carriers, whole blood, blood fractions, bone marrow aspirate, concentrated bone marrow aspirate, and mixtures thereof. Non-limiting examples of blood fractions include serum, plasma, platelet-rich plasma, concentrated platelet-rich plasma, platelet-poor plasma, and concentrated platelet poor plasma.

In some embodiments, the injectable and/or moldable implant is porous to allow influx of at least bone and/or cartilage cells therein. By "porous," it is meant that the implant has a plurality of pores. The pores of the implant are a size large enough to allow influx of blood, other bodily fluid, and progenitor and/or bone and/or cartilage cells into the interior to guide the process of tissue formation in vivo in three dimensions.

In some embodiments, the injectable and/or moldable implant comprises pores having a pore size from about 1 micron to about 500 microns. In some embodiments, the pore size is from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 440, 450, 460, 470, 480, 490 to about 500 microns.

In some embodiments, the injectable and/or moldable implant has a porosity of at least about 30%, at least about 50%, at least about 60%, at least about 70%, at least about 90% or at least about 95%, or at least about 99%. The pores may support ingrowth of cells, formation or remodeling of bone, cartilage and/or vascular tissue.

In some embodiments, the moldable implant can be molded by the surgeon to the desired shape to fit the tissue or bone defect. In some embodiments, the moldable implant has a size of from about 5 mm to about 500 mm. In some embodiments, the moldable implant has a size of about from about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 440, 450, 460, 470, 480, 490 to about 500 mm.

Additional Biodegradable Polymers

In some embodiments, the injectable and/or moldable implant in addition to alginate or as an alternative to alginate comprises one or more biodegradable polymers. In some embodiments, the biodegradable polymer is crosslinked. In an alternative embodiment, the injectable and/or moldable implant comprises human collagen, as well as recombinant collagen or combinations thereof. Examples of suitable collagen include, but are not limited to, human collagen type I, human collagen type II human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collage type XX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen further may comprise hetero- and homotrimers of any of the above-recited collagen types. In some embodiments, the collagen comprises hetero- or homotrimers of human collagen type I, human collagen type II, human collagen type III; or combinations thereof. In various embodiments, the collagen may be crosslinked.

In some alternate embodiments, the injectable and/or moldable implant comprises collagen-containing biomaterials from the implant market which, when placed in a bone defect, provide scaffolding around which the patient's new bone and/or cartilage will grow, gradually replacing the injectable and/or moldable implant as the target site heals. Examples of suitable carrier matrices may include, but are not limited to, the MasterGraft® Matrix produced by Medtronic Sofamor Danek, Inc., Memphis, Tenn.; MasterGraft® Putty produced by Medtronic Sofamor Danek, Inc., Memphis, Tenn.; Absorbable Collagen Sponge ("ACS") produced by Integra LifeSciences Corporation, Plainsboro, N.J.; bovine skin collagen fibers coated with hydroxyapatite, e.g., Healos®, marketed by Johnson & Johnson, USA; collagen sponges, e.g. Hemostagene® marketed by Coletica S A, France, or e.g., Helisat® marketed by Integra Life Sciences Inc., USA; and Collagraft® Bone Graft Matrix produced by Zimmer Holdings, Inc., Warsaw, Ind.

In some alternate embodiments, the collagen contains both soluble collagen and insoluble collagen fibers. The soluble collagen and insoluble collagen fibers can first be prepared separately, and then combined. Both the soluble collagen and the insoluble collagen fibers are derived from human sources.

In some embodiments, the injectable and/or moldable implant in addition to alginate or as an alternative to alginate comprises a biodegradable polymeric or non-polymeric material. In some embodiments, the injectable and/or moldable implant may include a biodegradable polymer. For example, the biodegradable polymer can comprise polyether ether ketone (PEEK). In some embodiments, the injectable and/or moldable implant may comprise one or more of poly (alpha-hydroxy acids), polyglycolide (PG), polyethylene glycol (PEG) conjugates of poly (alpha-hydroxy acids), polyorthoesters (POE), polyaspirins, polyphosphagenes, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, caprolactone, dextrans, vinylpyrrolidone, polyvinyl alcohol (PVA), PVA-g-PLGA, PEGT-PBT copolymer (polyactive), methacrylates, PEO-PPO-PAA copolymers, PLGA-PEO-PLGA, PEG-PLG, PLA-PLGA, poloxamer 407, PEG-PLGA-PEG triblock copolymers, POE, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyether ether ketone, polymethylmethacrylate, silicone, hyaluronic acid, or combinations thereof.

In some embodiments, the injectable and/or moldable implant alternatively or in addition comprises at least one biodegradable polymer comprising one or more of poly (lactide-co-glycolide) (PLGA), polylactide (PLA), polyglycolide (PGA), D-lactide, D,L-lactide, L-lactide, D,L-lactide-co-ε-caprolactone, L-lactide-co-εcaprolactone, D,L-lactide-co-glycolide-co-ε-caprolactone, poly(D,L-lactide-co-caprolactone), poly(D,L-lactide-co-caprolactone), poly(D-lactide-co-caprolactone), poly(D,L-lactide), poly(D-lactide), poly(L-lactide), poly(esteramide) or a combination thereof.

In some embodiments, the injectable and/or moldable implant alternatively or in addition to alginate comprises one or more polymers (e.g., PLA, PLGA, etc.) having a MW of from about 15,000 to about 150,000 Da or from about 25,000 to about 100,000 Da.

DBM/Additional Particles

In alternative embodiments, the implant comprises mineral particles, such as, for example, ceramics. In some embodiments, the particles in the implant comprise a resorbable ceramic, bone, synthetic degradable polymer, hyaluronic acid, chitosan or combinations thereof. In some embodiments, the particles comprise cortical, cancellous, and/or corticocancellous, allogenic, xenogeneic or transgenic bone tissue. The bone component can comprise, consist essentially of or consist of fully mineralized, partially demineralized, fully demineralized or combinations thereof. In some embodiments, the mineral particles comprise, consist essentially of or consist of bone powder, demineralized bone powder, porous calcium phosphate ceramics, hydroxyapatite, tricalcium phosphate, bioactive glass or combinations thereof.

In some alternative embodiments, the implant may comprise a resorbable ceramic (e.g., hydroxyapatite, tricalcium phosphate, bioglasses, calcium sulfate, etc.) tyrosine-derived polycarbonate poly (DTE-co-DT carbonate), in which the pendant group via the tyrosine—an amino acid—is either an ethyl ester (DTE) or free carboxylate (DT) or combinations thereof.

In some alternative embodiments, the implant may contain an inorganic material, such as an inorganic ceramic and/or bone substitute material. Exemplary inorganic materials or bone substitute materials include but are not limited to aragonite, dahlite, calcite, brushite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, BIOGLASS™ fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), or combinations or derivatives thereof.

In some embodiments, by including inorganic ceramics, such as for example, calcium phosphate, in the implant, this will act as a local source of calcium and phosphate to the cells attempting to deposit new bone. The inorganic ceramic also provides compression resistance and load bearing characteristics to the implant.

In some embodiments, the mineral particles in the implant comprise tricalcium phosphate and hydroxyapatite in a ratio of about 80:20 to about 90:10. In some embodiments, the mineral particles in the implant comprise tricalcium phosphate and hydroxyapatite in a ratio of about 70:30 to about 95:5. In some embodiments, the mineral particles in the implant comprise tricalcium phosphate and hydroxyapatite in a ratio of about 85:15.

In some embodiments, as discussed above, the implant contains demineralized bone material disposed therein. In some embodiments, the demineralized bone material can comprise demineralized bone, particles, powder, chips, triangular prisms, spheres, cubes, cylinders, shards, fibers or other shapes having irregular or random geometries. These can include, for example, "substantially demineralized," "partially demineralized," or "fully demineralized" cortical and cancellous bone. These also include surface demineralization, where the surface of the bone construct is substantially demineralized, partially demineralized, or fully demineralized, yet the body of the bone construct is fully mineralized. In some embodiments, the configuration of the bone material can be obtained by milling, shaving, cutting or machining whole bone.

In some alternative embodiments, the implant comprises elongated demineralized bone fibers having an average length to average thickness ratio or aspect ratio of the fibers from about 50:1 to about 1000:1. In overall appearance, the elongated demineralized bone fibers can be in the form of threads, narrow strips, or thin sheets. The elongated demineralized bone fibers can be substantially linear in appearance or they can be coiled to resemble springs. In some embodiments, the elongated demineralized bone fibers are of irregular shapes including, for example, linear, serpentine or curved shapes. The elongated bone fibers can be demineralized however some of the original mineral content may be retained when desirable for a particular embodiment.

Expandable Phase

In some embodiments, the implant may comprise a material, such as, for example, an expandable phase, to facilitate swelling of the implant. The expandable phase comprises polymers that swell upon taking in fluid (e.g., saline, water, bodily fluid, etc.), and thus increase the volume of the implant and which further holds the implant in position over time.

In some embodiments, the expandable phase comprises a range of from about 0.1% to about 20% based on the total weight of the implant. In some embodiments, the expandable phase comprises a range of from about 0.1% to about 10% based on the total weight of the implant. In some embodiments, the expandable phase comprises from about 0.1%, 0.25%, 0.5%, 0.75%, 1%, 2%, 3%, 4%, 5%, 6%, 7%, 8%, 9% or to about 10% based on the total weight of the implant.

In some embodiments, the expandable phase comprises polymers, monomers, starches, gums, poly(amino acids) or a combination thereof that swell upon contact with fluid (water, body fluids, etc.). In various embodiments, the amount of swelling can range from about 5 to about 100 percent, from about 5 to about 40 percent, or from about 5 to about 20 percent. The time to reach maximum swelling can be varied depending on the location and desired property of the implant. In practice, the time to reach maximum swelling can occur within a period of 5 days, 3 days, 2 days or within a period of 24 hours.

A suitable swellable material may include, for example, hydroxypropyl cellulose, hydroxypropyl methylcellulose, hydroxyethyl methylcellulose, carboxymethylcellulose, hydroxyethylcellulose and salts thereof, Carbopol, poly(hydroxyethylmethacrylate), poly(methoxyethylmethacrylate) poly(methoxyethoxy-ethylmethacrylate), polymethylmethacrylate (PMMA), methylmethacrylate (MMA), gelatin, polyvinyl alcohols, propylene glycol, PEG 200, PEG 300, PEG 400, PEG 500, PEG 550, PEG 600, PEG 700, PEG 800 PEG 900, PEG 1000, PEG 1450, PEG 3350, PEG 4500, PEG 8000 or combinations thereof. In some embodiments, the expandable phase includes gelling polymers including but not limited to cellulosic polymers, vinyl polymers, such as polyvinylpyrrolidone; acrylic polymers and copolymers, such as acrylic acid polymer, methacrylic acid copolymers, ethyl acrylate-methyl methacrylate copolymers, or the like; or mixtures thereof.

A non-limiting list of swellable materials which the expandable phase may comprise include polyvinyl alcohol (PVA), PVA modified with hydrophilic co-monomers, e.g., AMPS, PVA modified with fast crosslinking groups, e.g., NAAADA, PVA modified with polyvinylpyrroline (PVP), carboxymethylcellulose, polyethylene glycol (PEG), poly (vinyl ether), co-polymers of PVA and PEG, polypropylene glycol (PPG), co-polymers of PEG and PPG, co-polymers of PVA or PPG, polyacrylonitrile, hydrocolloids, e.g. agar, alginates, collagen, elastin, chitin, chitosan, gelatin, sugar, mannitol, or the like. In various embodiments, the swellable material includes, for example, poly(N-isopropylacrylamide-co-acrylic acid)-poly(L-lactic acid) (NAL); poly(N-isopropyl acrylamide) (PNIPAM) grafted to other polymers such as carboxymethylcellulose (CMC) copolymers or polymers including block copolymers and end-functionalized polymers, composites or copolymers containing thermosensitive poly(2-ethoxyethyl vinyl ether) and/or poly(hydroxyethyl vinyl ether) and/or (EOVE200-HOVE400), whose sol-gel transition temperature is 20.5° C.

In some embodiments, the expandable phase includes hyaluronic acid. In some embodiments, the expandable phase includes glycosaminoglycans. Non-limiting examples of glycosaminoglycans include chondroitin sulfate, dermatan sulfate, keratin sulfate, heparin, heparin sulfate, and hyaluronan. In some embodiments, the expandable phase includes mannitol, PEG, magnesium alginate or glycerol.

The swellable polymers may be crosslinked or lightly crosslinked hydrophilic polymers. Although these polymers may be non-ionic, cationic, zwitterionic, or anionic, in various embodiments, the swellable polymers are cationic or anionic. In various embodiments, the swellable polymer may contain a multiplicity of acid functional groups, such as carboxylic acid groups, or salts thereof. Examples of such polymers suitable for use herein include those which are prepared from polymerizable, acid-containing monomers, or monomers containing functional groups which can be converted to acid groups after polymerization. Examples of such polymers also include polysaccharide-based polymers such as carboxymethyl starch and cellulose, and poly(amino acid) polymers such as poly(aspartic acid). Some non-acid monomers may also be included, usually in minor amounts, in preparing the absorbent polymers. Such non-acid monomers include, for example, monomers containing the following types of functional groups: carboxylate or sulfonate esters, hydroxyl groups, amide groups, amino groups, nitrile groups, quaternary ammonium salt groups, and aryl groups (e.g. phenyl groups, such as those derived from styrene monomer). Other potential non-acid monomers include unsaturated hydrocarbons such as ethylene, propylene, 1-butene, butadiene, or isoprene.

In some embodiments, the expandable phase comprises substances which are capable of becoming freely permeable following hydration in aqueous fluids. Such substances include polysaccharides, such as gelatin, saccharose, sorbitol, mannanes, jaluronic acid, polyaminoacids, polyalcohols, polyglycols, or the like. In addition to the foregoing, the swellable polymer may also include additional excipients such as lubricants, flow promoting agents, plasticizers, and anti-sticking agents. For example, the expandable phase may further include polyethylene glycol, polyvinylpyrrolidone, talc, magnesium stearate, glyceryl behenate, stearic acid, or titanium dioxide.

In various embodiments, the particle size distribution of the expandable phase material may be about 10 micrometers, 13 micrometers, 85 micrometers, 100 micrometers, 151 micrometers, 200 micrometers and all subranges therebetween. In some embodiments, at least 75% of the particles have a size from about 10 micrometers to about 200 micrometers. In some embodiments, at least 85% of the particles have a size from about 10 micrometers to about 200 micrometers. In some embodiments, at least 95% of the particles have a size from about 10 micrometers to about 200 micrometers. In some embodiments, all of the particles have a size from about 10 micrometers to about 200 micrometers. In some embodiments, at least 75% of the particles have a size from about 20 micrometers to about 180 micrometers. In some embodiments, at least 85% of the particles have a size from about 20 micrometers to about 180 micrometers. In some embodiments, at least 95% of the particles have a size from about 20 micrometers to about 180 micrometers. In some embodiments, all of the particles have a size from about 20 micrometers to about 180 micrometers.

Lyophilization

In some embodiments, the DBM fibers, particles and chips are lyophilized. The lyophilization process typically includes sublimation of water from a frozen formulation under controlled conditions. Lyophilization can be carried out using standard equipment as used for lyophilization or vacuum drying. The cycle may be varied depending upon the equipment and facilities used for the fill and finish.

Initially, in some embodiments, the DBM is placed in a lyophilization chamber under a range of temperatures and then subjected to temperatures well below the freezing point of DBM, generally for several hours. After freezing is complete, the lyophilization chamber and the condenser are evacuated through vacuum pumps, the condenser surface having been previously chilled by circulating refrigerant. The condenser will have been chilled below the freezing point of the DBM. Additionally, evacuation of the chamber should continue until a pressure of about 50 mTorr to about 600 mTorr, preferably about 50 to about 150 mTorr is obtained.

The lyophilized DBM is then warmed under vacuum in the chamber and condenser. This usually will be carried out by warming the shelves within the lyophilizer on which the lyophilized DBM rests during the lyophilization process at a pressure ranging from about 50 mTorr to about 600 mTorr. The warming process will optimally take place very gradually, over the course of several hours. Complete drying can be accomplished by stabilization of vacuum, condenser temperature and lyophilized DBM shelf temperature. After the initial drying, the temperature of the lyophilized DBM can be increased and maintained for several hours. Once the drying cycle is completed, the pressure in the chamber can be slowly released to atmospheric pressure (or slightly below) with sterile, dry-nitrogen gas (or equivalent gas).

In some embodiments, after lyophilization, the DBM is from about 95 to about 99.5% free of moisture. In various embodiments, the DBM is from about 95, 95.5, 96, 96.5, 97, 97.5, 98, 98.5, 99, to about 99.5% free of moisture. In some embodiments, the DBM has about 0.5% to about 5% moisture content remaining after lyophilization. In various embodiments, the DBM has from about 0.5, 1, 1.5, 2, 2.5, 3, 3.5, 4, 4.5 to about 5% moisture content remaining after lyophilization. Lyophilized DBM is stable and can be stored at a wide range of temperatures. Lyophilized DBM can be stored at or below 30° C., for example, refrigerated at 4° C., or at room temperature (e.g., approximately 25° C.).

Method of Making

In some embodiments, a method of making an injectable or moldable implant is provided. The method comprises mixing lyophilized demineralized bone matrix (DBM) being in fiber and particle forms in an amount of about 28% based on a total weight of the implant, or DBM in fiber, particle and chip forms in an amount of about 30% based on the total weight of the implant with an aqueous liquid comprising an alginate so as to uniformly distribute the DBM within the alginate to form the injectable or moldable implant.

In some embodiments, the alginate is in an amount of about 1 wt. % to about 10 wt. % of the total weight of the implant or in an amount of about 3 wt. % to about 20 wt. % of the total weight of the implant.

In some embodiments, the aqueous liquid comprises phosphate buffered saline. In some embodiments, the phosphate buffered saline is in an amount of about 50 wt. % to about 70 wt. % of the total weight of the implant or in an amount of about 40 wt. % to about 60 wt. % of the total weight of the implant.

In some embodiments, before the DBM is mixed with the aqueous liquid, the aqueous liquid is mixed with the alginate and formed into a gel, and the gel is irradiated to sterilize the gel. In some embodiments, the mixing step is performed aseptically. In some embodiments, sterile filtered water is mixed concurrently with the DBM into the aqueous liquid. In some embodiments, the sterile filtered water is in an amount of from 1 to about 50 wt. % based on the total weight of the moldable implant.

In some embodiments, the method further comprises loading the injectable implant into a syringe after the implant is formed and inserting the syringe into a pre-sterilized foil pouch. In some embodiments, the method further comprises inserting the moldable implant into a pre-sterilized foil pouch.

In some embodiments, before administration to a patient, in some instances, the biodegradable polymer (e.g., alginate) can be subjected to one or more additional operations such as heating, lyophilizing and/or crosslinking. In this regard, crosslinking can be used to improve the strength of the implant. Crosslinking can be achieved, for example, by chemical reaction, the application of energy such as radiant energy (e.g., UV light or microwave energy), drying and/or heating and dye-mediated photo-oxidation; dehydrothermal treatment; enzymatic treatment or others.

In some embodiments, a chemical crosslinking agent is used. Examples of suitable crosslinking agents include those that contain bifunctional or multifunctional reactive groups, and which react with the implant. Chemical crosslinking can be introduced by exposing the implant to a chemical crosslinking agent, either by contacting it with a solution of the chemical crosslinking agent or by exposure to the vapors of the chemical crosslinking agent. The resulting material can then be washed to remove substantially all remaining amounts of the chemical crosslinker if needed or desired for the performance or acceptability of the final implant.

Suitable chemical crosslinking agents include mono- and dialdehydes, including glutaraldehyde and formaldehyde; polyepoxy compounds such as glycerol polyglycidyl ethers, polyethylene glycol diglycidyl ethers and other polyepoxy and diepoxy glycidyl ethers; tanning agents including polyvalent metallic oxides such as titanium dioxide, chromium dioxide, aluminum dioxide, zirconium salt, as well as organic tannins and other phenolic oxides derived from plants; chemicals for esterification or carboxyl groups followed by reaction with hydrazide to form activated acyl azide functionalities in the collagen; dicyclohexyl carbodiimide and its derivatives as well as other heterobifunctional crosslinking agents; hexamethylene diisocyante; and/or sugars, including glucose, will also crosslink the implant.

In some embodiments, radiographic markers can be included on the implant to permit the user to position it accurately into the target site of the patient. These radiographic markers will also permit the user to track movement and degradation of the implant at the site over time. In this embodiment, the user may accurately position the implant in the site using any of the numerous diagnostic imaging procedures. Such diagnostic imaging procedures include, for example, X-ray imaging or fluoroscopy. Examples of such radiographic markers include, but are not limited to, ceramics, barium, phosphate, bismuth, iodine, tantalum, tungsten, and/or metal beads or particles. In various embodiments, the radiographic marker could be a spherical shape or a ring around the implant.

In some embodiments, the implant can be administered to the target site by passing it through a "cannula" or "needle" that can be a part of a delivery device e.g., a syringe, a gun delivery device, or any medical device suitable for the delivery of the implant to a targeted organ or anatomic region. The cannula or needle of the device is designed to cause minimal physical and psychological trauma to the patient.

The implant may be used to repair bone and/or cartilage at a target tissue site, e.g., one resulting from injury, defect brought about during the course of surgery, infection, malignancy or developmental malformation. The implant can be utilized in a wide variety of orthopedic, periodontal, neurosurgical, oral and maxillofacial surgical procedures such as the repair of simple and/or compound fractures and/or non-unions; external and/or internal fixations; joint reconstructions such as arthrodesis; general arthroplasty; cup arthroplasty of the hip; femoral and humeral head replacement; femoral head surface replacement and/or total joint replacement; repairs of the vertebral column including spinal fusion and internal fixation; tumor surgery, e.g., deficit filling; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay implantable matrices; implant placement and revision; sinus lifts; cosmetic procedures; etc. Specific bones which can be repaired or replaced with the implant herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal and/or metatarsal bones.

Additional Therapeutic Agents

In some embodiments, the implant further comprises one or more additional therapeutic agents including one or more growth factors, statins, etc. Isolated osteoinductive agents that are included within an implant are typically sterile. In a non-limiting method, sterility is readily accomplished for example by filtration through sterile filtration membranes 0.2 micron membranes or filters). In one embodiment, the implant includes osteoinductive agents comprising one or more members of the family of Bone Morphogenetic Proteins ("BMPs"). BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-14 (GDF-5), BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

Indeed, the osteoinductive factors are the recombinant human bone morphogenetic proteins (rhBMPs) because they are available in unlimited supply and do not transmit infectious diseases. In some embodiments, the bone morphogenetic protein is a rhBMP-2, rhBMP-4, rhBMP-7, or heterodimers thereof.

Recombinant BMP-2 can be used at a concentration of about 0.4 mg/mL, to about 10.0 mg/mL, preferably near 1.5 mg/mL. However, any bone morphogenetic protein is contemplated including bone morphogenetic proteins designated as BMP-1 through BMP-18. BMPs are available from Wyeth, Cambridge, Mass. and the BMPs and genes encoding them may also be prepared by one skilled in the art as described in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al. All osteoinductive factors are contemplated whether obtained as above or isolated from bone. Methods for isolating bone morphogenetic protein from bone are described, for example, in U.S. Pat. No. 4,294,753 to Urist and Urist et al., 81 PNAS 371, 1984.

In addition to the above, the implant may include one or more members from the TGF-β superfamily. For example, the implant may include AMH, ARTN, GDF1, GDF10, GDF11, GDF15, GDF2, GDF3, GDF3A, GDF5, GDF6, GDF7, GDF8, GDF9, GDNF, INHA, INHBA, INHBB, INHBC, INHBE, LEFTY1, LEFTY2, MSTN, NODAL, NRTN, PSPN, TGFB1, TGFB2, TGFB3, FGF, basic FGF, VEGF, insulin-like growth factor, EGF, PDGF, nerve growth factor or combinations thereof.

The growth factors of the present application may be disposed on or in the implant with other therapeutic agents. For example, the growth factor may be disposed on or in the implant by electrospraying, ionization spraying or impregnating, vibratory dispersion (including sonication), nozzle spraying, compressed-air-assisted spraying, brushing and/or pouring.

Exemplary therapeutic agents include but are not limited to IL-1 inhibitors, such Kineret® (anakinra), which is a recombinant, non-glycosylated form of the human interleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as antioxidants, such as dithiocarbamate, and other compounds, such as, for example, sulfasalazine, statins or the like.

Examples of therapeutic agents suitable for use also include, but are not limited to, an anti-inflammatory agent, analgesic agent, or osteoinductive growth factor or a combination thereof.

In some embodiments, additives are provided that can be disposed on or in the implant to enhance the DBM osteoinductive, osteoconductive, and/or osteopromotive activity. The additives include, but are not limited to ascorbic acid in an amount of from about 0.001 wt. % to about 3 wt. % based on the total weight of the implant, dexamethasone in an amount of from about 0.0001 wt. % to about 0.1 wt. % based on the total weight of the implant, β-glycerophosphate in an amount of from about 0.001 wt. % to about 3 wt. % based on the total weight of the implant, L-arginine in an amount of from about 0.001 wt. % to about 3 wt. % based on the total weight of the implant, L-ascorbic acid-2-phosphate in an amount of from about 0.001 wt. % to about 3 wt. % based on the total weight of the implant, nano-hydroxyapatite in an amount of from about 0.1 wt. % to about 30 wt. % based on the total weight of the implant, or a combination thereof. The additive can also include zinc chloride in an amount of from about 0.001 wt. % to about 3 wt. % based on the total weight of the implant.

Kits

The implant and/or the medical device to administer it may be sterilizable. The implant is aseptically processed (e.g., not requiring terminal irradiation). In some embodiments, the implant may be packaged in a moisture resistant sterile package. In use, the surgeon removes one or all components from the sterile package for use.

In various embodiments, a kit is provided comprising the implant. The kit may include additional parts along with the implant combined together to be used to administer the implant (e.g., wipes, needles, syringes, mixing syringe or other mixing device, etc.). The kit may include the implant in a first compartment. The second compartment may include a vial holding the carrier and any other instruments needed for the delivery. A third compartment may include gloves, drapes, wound dressings and other procedural supplies for maintaining sterility of the implanting process, as well as an instruction booklet, which may include a chart that shows how to administer the implant after reconstituting it. A fourth compartment may include additional needles and/or sutures. Each tool may be separately packaged in a plastic pouch that is sterilized. A fifth compartment may include an agent for radiographic imaging. A cover of the kit may include illustrations of the implanting procedure and a clear plastic cover may be placed over the compartments to maintain sterility.

These and other aspects of the present application will be further appreciated upon consideration of the following Examples, which are intended to illustrate certain particular embodiments of the application but are not intended to limit its scope, as defined by the claims.

EXAMPLES

A predicate bone graft device contains demineralized bone matrix (DBM) particles in a sodium alginate/bovine collagen carrier. The product is processed such that terminal sterilization is required, which is applied through exposure to E-beam radiation at 25-30 kGy. A new bone graft putty, which contains DBM fibers in a sodium alginate carrier was made. This study was undertaken to compare the new putty processed either aseptically (i.e. not requiring terminally irradiation), or following E-beam irradiation, by assessing performance in a rat osteoinductivity (OI) model and in a rat two-level posterolateral spine fusion (PLF) model.

An aseptically processed (e.g., not requiring terminal irradiation) putty implant and an E-beam irradiated putty implant were compared to each other by assessing performance in a rat osteoinductivity (OI) model and in a rat two-level posterolateral spine fusion (PLF) model. Both implants contained the same ingredients such as DBM in fiber and particle form disposed in a sodium alginate carrier.

Example 1

Manufacture of the Implants

1. Manufacture of Irradiated PLF Implants:

Implant putty samples were created in a biosafety cabinet by hand mixing components shown in Table 1 below. 0.6 cc samples were loaded into 1 cc syringes and packaged in foil pouches, and irradiated with E-beam at 27 kilograys (kGy).

TABLE 1

Recipe for Implant Putty

| Component | Composition by Weight |
|---|---|
| Demineralized bone matrix (DBM) | 25% |
| Sterile filtered water | 38% |
| Sterile sodium alginate | 6% |
| Phosphate buffered saline (PBS) | 32% |

2. Manufacture of Aseptic PLF Implants:

The alginate and PBS components from Table 1 were manually mixed until homogeneous. The resulting gel was loaded into a 12 cc syringe and irradiated with E-beam at 27 kGy. A sterile environment was created in a biosafety cabinet, and the sterile gel was aseptically mixed with the other two components from Table 1 for a period of time. 0.6 cc samples were loaded into 1 cc syringes and packaged in pre-sterilized foil pouches.

3. Isolation of DBM from Irradiated and Aseptic OI Implants:

Leftover irradiated and aseptic materials from the PLF study implant manufacturing were placed in separate 50 mL centrifuge tubes. 30 cc of sterile water was added to each tube and implant materials were fully suspended by vortexing the centrifuge tube. DBM was recovered from the suspension by centrifugation at 3,800 revolutions per minute (RPM) for 5 minutes. The process of resuspension and centrifugation was repeated two additional times such that the viscosity of supernatant water following centrifugation was indistinguishable from deionized (DI) water. 0.2 cc samples were then loaded into ice syringes and packaged in pre-sterilized foil pouches.

Example 2

Rat 2-Level PLF Study

Twelve Athymic Nude rats were utilized in the study. The rats were divided into two groups of six. Under general anesthesia and aseptic conditions, surgical decortication of the dorsal surfaces of the transverse processes of the 3rd, 4th and 5th lumbar vertebrae (L3-5) was performed in all animals. Test materials were placed on the paraspinal beds bridging the decorticated transverse processes, followed by standard wound closure. Spine radiography was performed immediately after surgery, four weeks after surgery, and prior to necropsy at about eight weeks after surgery. Appropriate post-operative analgesia and animal care was provided. Animals were sacrificed eight weeks after the surgery was performed. The lumbar spines were radiographed, explanted, palpated for motion in the operated segments during the necropsy and then saved in 10% neutral buffered formalin. The results of the groups are listed in FIG. 3.

It was concluded that irradiated implants fused 8 of 24 unilateral segments (33%) as shown in FIG. 5, while aseptic implants fused 24 of 24 unilateral segments (100%) by manual palpation and radiographically, as shown in FIG. 4. FIG. 4 illustrates an x-ray of rat subjects in group 1 that were administered the injectable aseptic implant and their progress at 2 weeks, 4 weeks, and 8 weeks after implantation. FIG. 5 illustrates an x-ray of rat subjects from group 2 that were administered the irradiated moldable putty and their progress at 2 weeks, 4 weeks, and 8 weeks after implantation. Greater consolidation and organization of new bone was observed radiographically in the aseptic group as opposed to the irradiated treatment group.

Example 3

Rat OI Study

Four athymic male rats were used in this study with four implant sites per test sample. Each animal received two intermuscular implants in the *Adductor Brevis: Semimembranosus* muscles. The samples were randomized so that no animal received the same lot in both the left and right implant sites. The animals were anesthetized and prepared for surgery. Pockets were created using sharp and blunt dissection in the muscle. After the incision over the implant site was made, the sample was placed into the muscle pocket, and then the pocket and skin were sutured closed. The animals were in-life for 28 days and observed daily for abnormal general health status. At the end of the study duration, animals were sacrificed and the implants were removed. The tissues were fixed in 10% neutral buffered formalin prior to routine decalcification and processed into paraffin blocks. At least four sections were cut from the block, mounted on slides and stained with hematoxylin and eosin (H&E). Slides were viewed under a microscope and interpreted by a pathologist; the histopathology is semi-quantitative. A score was assigned to each implant site as either positive or negative for evidence of new bone formation elements.

Results showed that an average OI score for the aseptic group (2.25) was higher than for the irradiated group (1.0).

In conclusion, aseptically processed putty implants demonstrated higher performance in a rat 2-level posterolateral fusion model. Performance in this model aligned with higher osteoinductivity of the DBM within the aseptic final product samples verse irradiated final product samples.

Example 4

An injectable putty was made that had similar handling to the predicate irradiated putty. The putty contained the following:

| Component | Composition by Weight | Component Characteristic |
|---|---|---|
| Demineralized bone matrix (DBM) Lyophilized | 28% | DBM 50:50 fibers to particles. Fibers have a size 1 mm and above. Particles have a size of 100 microns to 1000 microns. |
| Sterile dry sodium alginate | 6% | Particles have a size of 100 microns to 1000 microns. |
| Phosphate buffered saline (PBS) | 66% | |

The injectable putty has a higher percentage of diluent (e.g., PBS) and having DBM fibers in it leads to improved osteoconductivity compared to using particles alone.

Example 5

A moldable implant was made that contained the following:

| Component | Composition by Weight | Component Characteristic |
|---|---|---|
| Demineralized bone matrix (DBM) Lyophilized | 30% | 33:33:33 DBM fibers, chips, and particles. Fibers have a size 1 mm and above. Particles have a size of 100 microns to 1000 microns. |

-continued

| Component | Composition by Weight | Component Characteristic |
|---|---|---|
| | | Chips have a size of 1 micron to 4 microns. |
| Sterile dry sodium alginate | 14% | Particles have a size of 100 microns to 1000 microns |
| Phosphate buffered saline (PBS) | 56% | |

The moldable implant has a higher percentage of DBM in fibers, chips and particles and lower percentage of diluent (e.g., PBS). DBM fibers lead to improved osteoconductivity compared to using particles alone.

Example 6

Rabbit PLF Study

1. Preclinical Study Model:

An un-instrumented single level rabbit posterolateral lumbar spinal fusion model was used in this study. Procedures were conducted on skeletally mature New Zealand White rabbits.

2. Specimen Preparation:

For Groups 1 and 2, the putty and moldable implants were provided in sterile form in pre-packed syringes containing approximately 3 cc of material that were ready to use. The Group 1 putty contained lyophilized DBM comprising a ratio of fibers to particles of 50:50, sterile dry sodium alginate, PBS and sterile water. The Group 2 moldable implant contained lyophilized DBM comprising a ratio of fibers, chips to particles of 33:33:33, sterile dry sodium alginate, PBS and sterile water. In Groups 3 and 4, 1.25-1.5 cc of test material putty and moldable implants were discharged into a sterile weigh boat, combined with an equal volume of autograft morsels and thoroughly mixed. The mixture was loaded into an open barrel 3 cc syringe to measure the volume prior to implantation. Therefore, the Group 3 material contained a combination product comprising the injectable putty of Group 1 and 50% autograft, and the Group 4 material contained a combination product comprising the moldable implant of Group 2 and 50% autograft. For Group 5, the predicate irradiated putty material containing demineralized bone matrix (DBM) particles in a sodium alginate/bovine collagen carrier, and the control autograft of Group 6 was provided in a sterile, ready-to-use form.

3. Spine Fusion Procedure:

The dorsal surfaces of the transverse processes of L4 and L5 were decorticated. Implants were deployed such that they were in contact with and spanned the distance between the decorticated L4 and L5 transverse processes bilaterally.

4. Autograft Harvest:

Autograft from the iliac crests was harvested bilaterally from Group 3, Group 4, and Group 6 animals. Harvested autograft was morselized using Rongeur forceps.

5. Necropsy:

Coronal x-rays were taken at necropsy. The lumbar spines were explanted, and the operated segments were palpated for motion. Operative sites were graded as either "F" for fused or "M" for motion.

Figure 8:
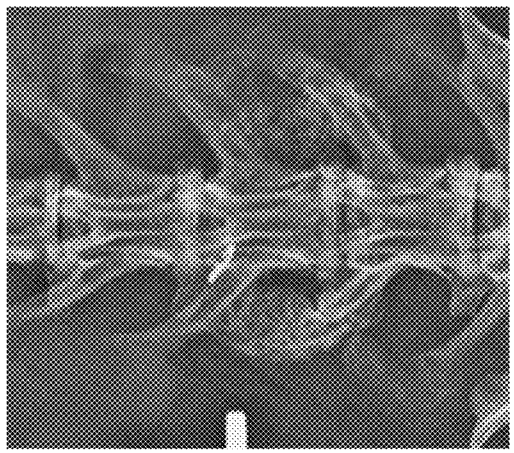
FIG. 8 illustrates an x-ray of rabbit subjects in Group 2 that were administered the moldable implant.
Figure 8:
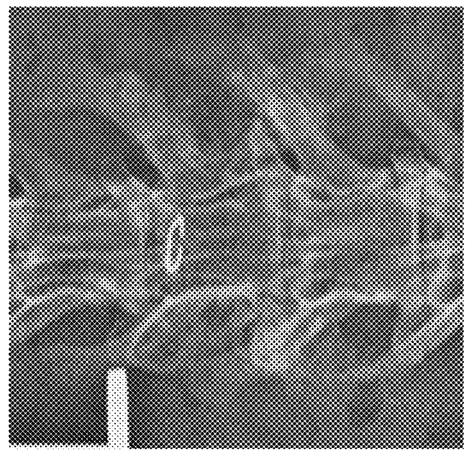
Figure 8:
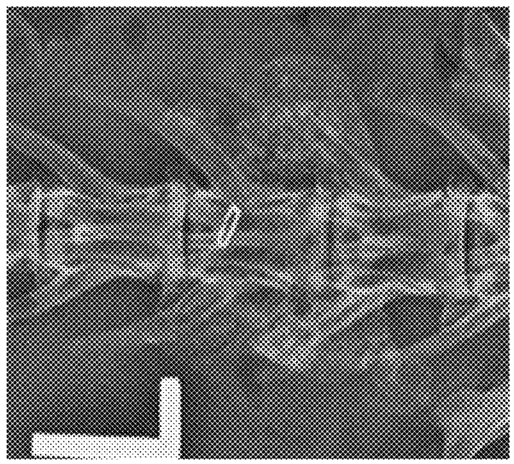
Figure 8:
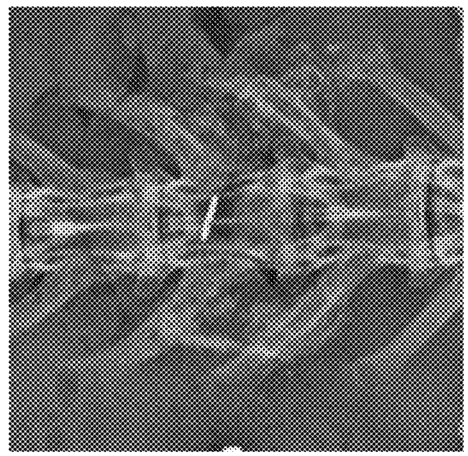
Figure 8:
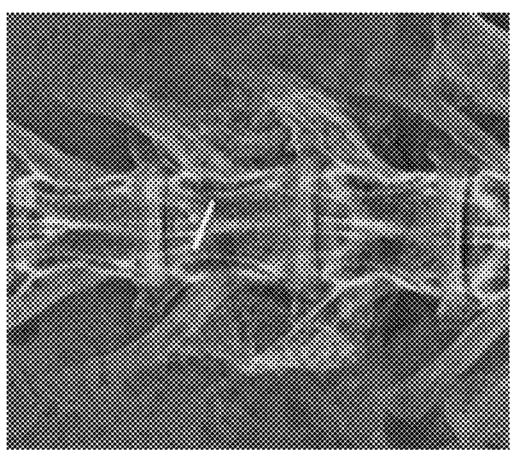

6. Results:

The results of this study are illustrated in FIGS. 6-8. Group 1 results showed bilateral fusion in 3 out of 6 segments and unilateral fusion in 6 out of 12 segments, as shown in FIG. 7. Group 2 results showed bilateral fusion in 0 out of 6 segments and unilateral fusion in 1 out of 12 segments, as shown in FIG. 8. Group 3 results showed bilateral fusion in 3 out of 6 segments and unilateral fusion in 6 out of 12 segments. Group 4 results showed bilateral fusion in 1 out of 6 segments and unilateral fusion in 2 out of 12 segments. Group 5 results showed bilateral fusion in 0 out of 6 segments and unilateral fusion in 0 out of 12 segments. Group 6 results showed bilateral fusion in 3 out of 6 segments and unilateral fusion in 6 out of 12 segments.

All patent and non-patent publications cited in this disclosure are incorporated herein in to the extent as if each of those patent and non-patent publications was incorporated herein by reference in its entirety. Further, even though the disclosure herein has been described with reference to particular examples and embodiments, it is to be understood that these examples and embodiments are merely illustrative of the principles and applications of the present disclosure. It is therefore to be understood that numerous modifications may be made to the illustrative embodiments and that other arrangements may be devised without departing from the spirit and scope of the present disclosure as defined by the following claims.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An injectable implant configured to fit at or near a bone defect to promote bone growth, the injectable implant comprising lyophilized demineralized bone matrix (DBM) being in fiber and particle forms in a ratio of 50:50 fibers to particles; alginate; and a liquid carrier, wherein the DBM is in an amount of about 25 wt. % of a total weight of the injectable implant, the alginate is in an amount of from about 1 wt. % to about 10 wt. % of the total weight of the injectable implant, and the injectable implant does not contain any collagen in addition to the demineralized bone matrix (DBM), and the fibers have an aspect ratio of about 50:1 to about 1000:1, wherein the injectable implant is an aseptically processed injectable implant.

2. The injectable implant of claim 1, wherein the defect is a bone void and the injectable implant is a bone void filler that is an injectable putty form.

3. The injectable implant of claim 1, wherein the fiber form has a size of from about 1 to about 7 mm, and the particle form has a size of from about 100 microns to about 1000 microns.

4. The injectable implant of claim 1, wherein the injectable implant further comprises sterile water and is in a putty form.

5. The injectable implant of claim 1, wherein the alginate is a sterile sodium alginate powder and the alginate has a particle size of from about 100 to about 1,000 microns.

6. The injectable implant of claim 1, wherein the injectable implant further comprises at least one viscosity enhancing agent, a biodegradable polymer, a mineral particle or a therapeutic agent.

7. The injectable implant of claim 1, wherein the injectable implant has a modulus of elasticity in a range of about 150 to about 2200 Pascals.

8. A moldable implant configured to fit at or near a bone defect to promote bone growth, the moldable implant comprising lyophilized demineralized bone matrix (DBM) being in fiber and particle forms in a ratio of 33:33, the DBM being in the moldable implant in an amount of about 25 wt. % based on a total weight of the moldable implant; and the moldable implant comprising an alginate in an amount of about 6 wt. % based on the total weight of the moldable implant, wherein the moldable implant has a modulus of elasticity in a range of about 150 to about 2200 Pascals and does not contain any collagen in addition to the demineralized bone matrix (DBM), wherein the moldable implant is an aseptically processed moldable implant and provides a 100% spinal fusion at a surgical site.

9. The moldable implant of claim 8, wherein the defect is a bone void and the moldable implant is a bone void filler being in a putty form.

10. The moldable implant of claim 8, wherein the fiber form has a size of from about 1 to about 7 mm, the particle form has a size of from about 100 microns to about 1000 microns, and optionally further comprises a chip form having a size of from about 1 to about 4 mm.

11. The moldable implant of claim 8, wherein the alginate is a sterile sodium alginate powder and the alginate has a particle size of from about 100 to about 1,000 microns.

12. The moldable implant of claim 8, wherein the moldable implant further comprises at least one viscosity enhancing agent, a biodegradable polymer, a mineral particle, or a therapeutic agent.

* * * * *